(12) United States Patent
Zippin

(10) Patent No.: US 11,680,264 B2
(45) Date of Patent: Jun. 20, 2023

(54) METHODS OF MODULATING MELANOSOME PH AND MELANIN LEVEL IN CELLS

(71) Applicant: Cornell University, Ithaca, NY (US)

(72) Inventor: Jonathan Zippin, Scarsdale, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/314,203

(22) PCT Filed: Jun. 30, 2017

(86) PCT No.: PCT/US2017/040428
§ 371 (c)(1),
(2) Date: Dec. 28, 2018

(87) PCT Pub. No.: WO2018/006039
PCT Pub. Date: Jan. 4, 2018

(65) Prior Publication Data
US 2019/0256856 A1 Aug. 22, 2019

Related U.S. Application Data

(60) Provisional application No. 62/480,189, filed on Mar. 31, 2017, provisional application No. 62/357,606, filed on Jul. 1, 2016.

(51) Int. Cl.
| | |
|---|---|
| *C12N 15/113* | (2010.01) |
| *A61P 17/00* | (2006.01) |
| *A61K 31/4184* | (2006.01) |
| *A61K 31/506* | (2006.01) |
| *A61K 31/713* | (2006.01) |
| *A61K 31/7076* | (2006.01) |

(52) U.S. Cl.
CPC ...... *C12N 15/1137* (2013.01); *A61K 31/4184* (2013.01); *A61K 31/506* (2013.01); *A61K 31/7076* (2013.01); *A61K 31/713* (2013.01); *A61P 17/00* (2018.01); *C12N 2310/14* (2013.01)

(58) Field of Classification Search
CPC ............. A61K 31/713; A61K 31/4184; C12N 2310/14
See application file for complete search history.

(56) References Cited

U.S. PATENT DOCUMENTS

| 8,822,540 B2* | 9/2014 | Brooks ................... A61Q 5/00 |
| | | 514/612 |
| 9,388,250 B2* | 7/2016 | Buck ..................... A61K 31/427 |
| 2005/0202001 A1 | 9/2005 | Koo et al. |
| 2007/0197482 A1 | 8/2007 | McPhee et al. |
| 2011/0305640 A1 | 12/2011 | Buck et al. |

OTHER PUBLICATIONS

Lee et al (J. Biol. Chem. 280(48): 41353-41358, 2011) (Year: 2011).*
Dessinioti (Experimental Dermatology, 18, 741-749, 2009) (Year: 2009).*
Xu et al (Biomolecules 2015, 5, 1122-1142) (Year: 2015).*
Ota et al (J Invest Dermatol 137(5) Supplement 1, May 2017) (Year: 2017).*
Ancans et al., "Activation of melanogenesis by vacuolar type H+-ATPase inhibitors in amelanotic, tyrosinase positive human and mouse melanoma cells," *FEBS Letters*, 478: 57-60 (2000).
Cheli et al., "αMSH and Cyclic-AMP Elevating Agents Control Melanosome pH through a Protein Kinase A-independent Mechanism," *J. Bio. Chem.*, jbc-M109 284(28): 18699-18706 (Jul. 10, 2009).
Pastor-Soler et al., "Bicarbonate-regulated adenylyl cyclase (sAC) is a Sensor That Regulates pH-dependent V-ATPase recycling," J. Bio. Chemn., 278(49): 49523-49529 (Dec. 5, 2003).
U.S. Patent Office, International Search Report in International Patent Application No. PCT/US2017/040428, 5 pp. (dated Nov. 9, 2017).
U.S. Patent Office, Written Opinion in International Patent Application No. PCT/US2017/040428, 14 pp. (dated Nov. 9, 2017).
Zhou et al., "Mammalian pigmentation is regulated by a distinct cAMP-dependent mechanism that controls melanosome pH," *Science Signaling*, 11(555): 1-12 (Nov. 6, 2018).

\* cited by examiner

*Primary Examiner* — Richard A Schnizer
(74) *Attorney, Agent, or Firm* — Leydig, Voit & Mayer, Ltd.

(57) ABSTRACT

The invention is directed to compositions and methods for increasing the pH of a melanosome in a melanocyte, darkening skin or hair pigmentation, or treating a disease associated with decreased melanin comprising administering a soluble adenylyl cyclase (sAC) inhibitor and/or an exchange protein activated by cyclic AMP (EPAC) inhibitor to the melanocyte. The invention also provides compositions and methods for decreasing the pH of a melanosome in a melanocyte, lightening skin or hair pigmentation, or treating a disease associated with increased melanin comprising administering a sAC activator and/or an EPAC activator to the melanocyte.

18 Claims, 22 Drawing Sheets

Figure 1A:
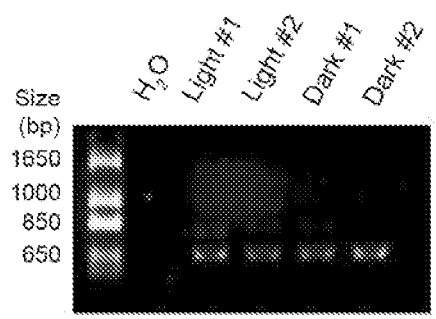

Specification includes a Sequence Listing.

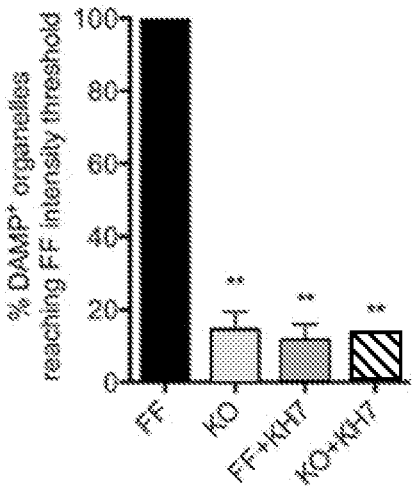 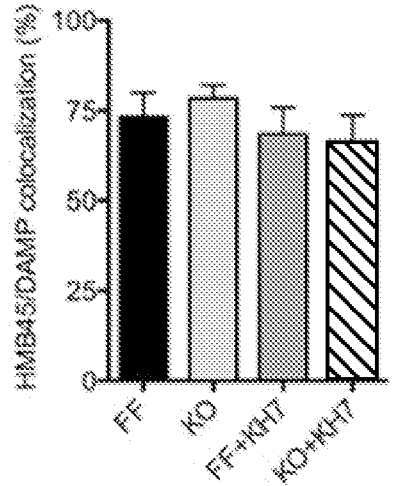 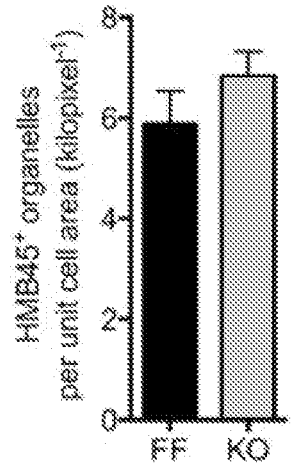
FIG. 4A     FIG. 4B     FIG. 4C
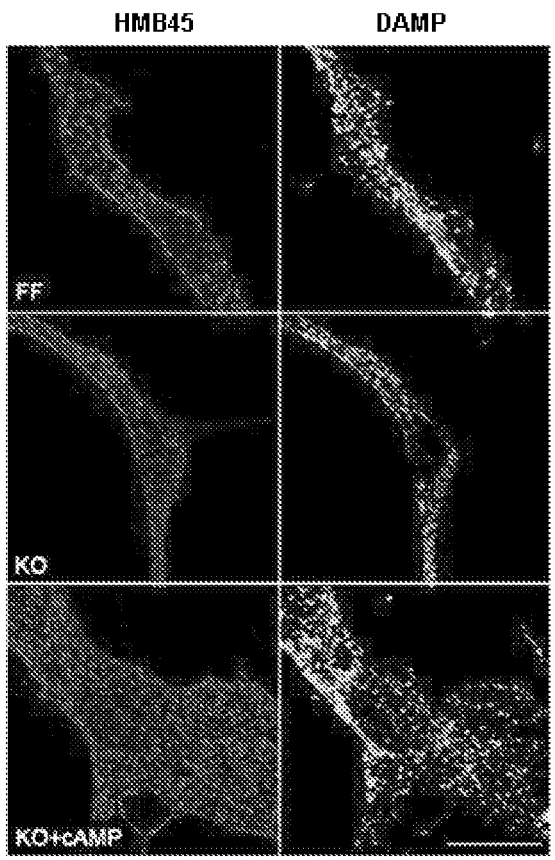 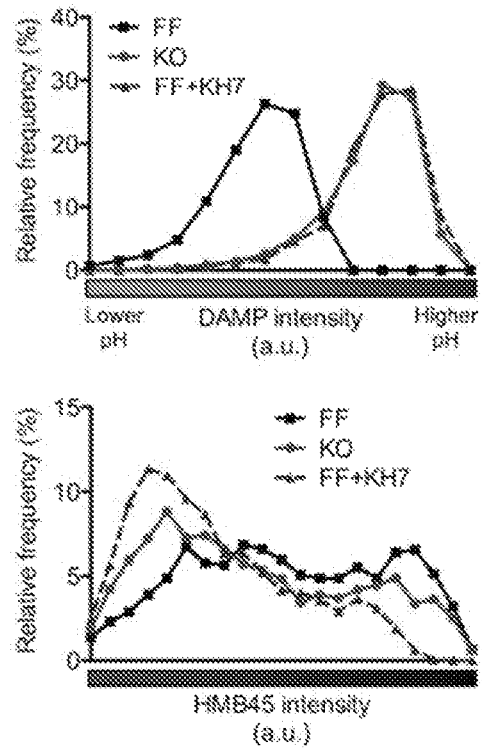
FIG. 4D     FIG. 4E

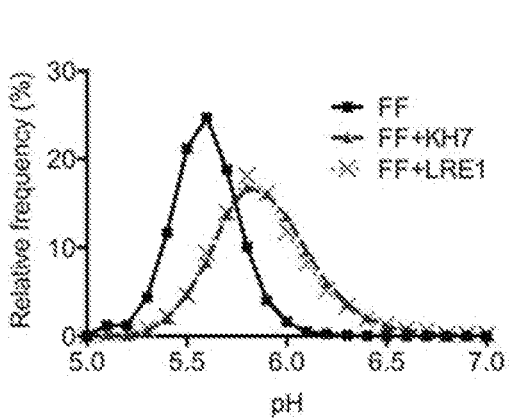
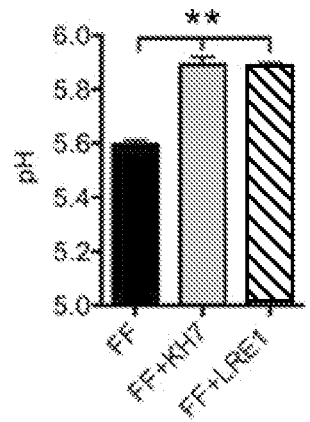
FIG. 5A  FIG. 5B
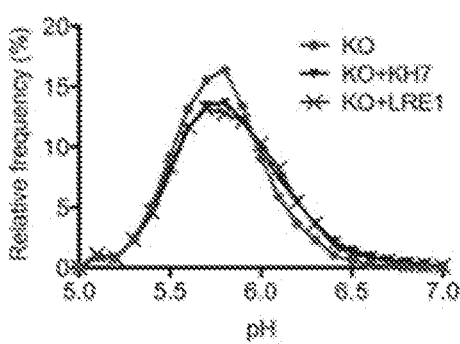
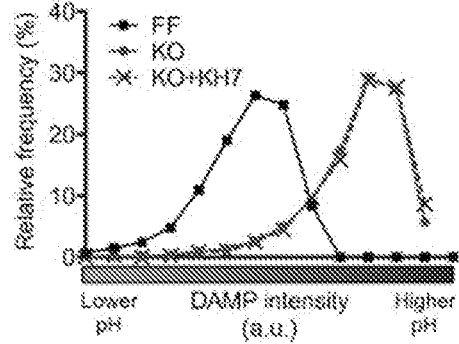
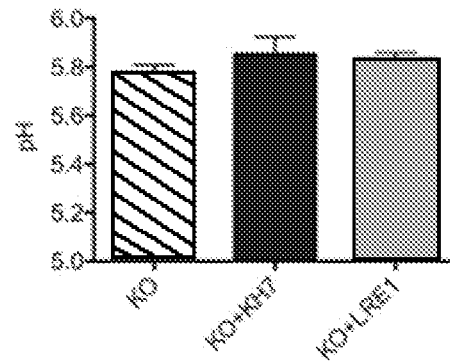
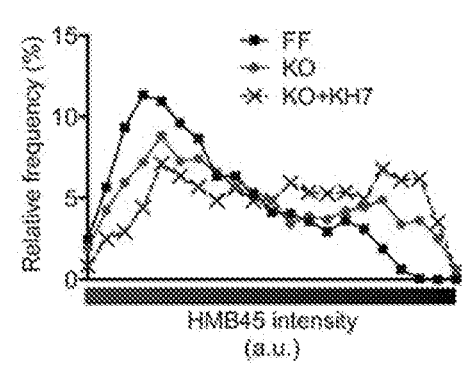
FIG. 5C  FIG. 5D

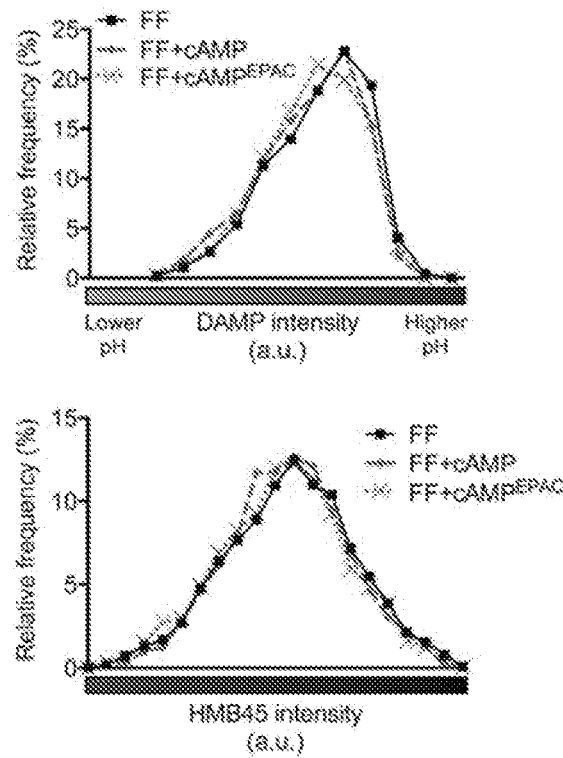
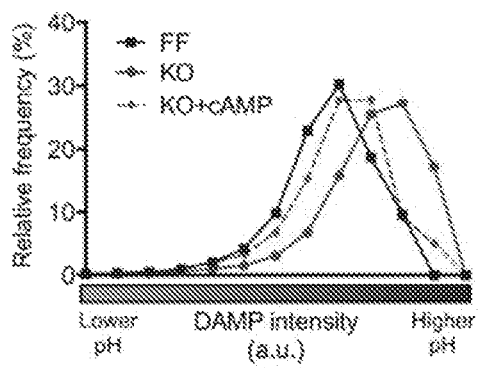
FIG. 7A
FIG. 7B
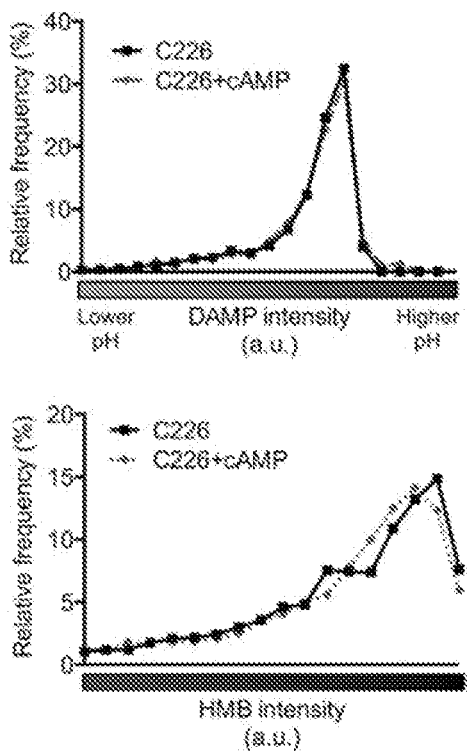
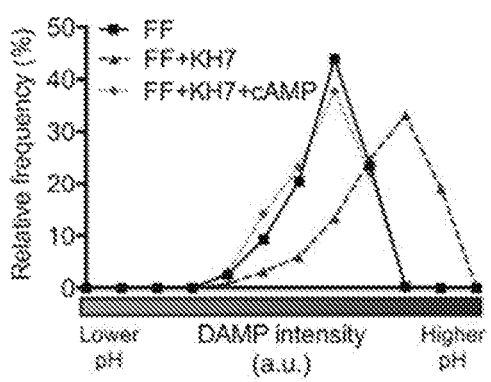
FIG. 7C
FIG. 7D

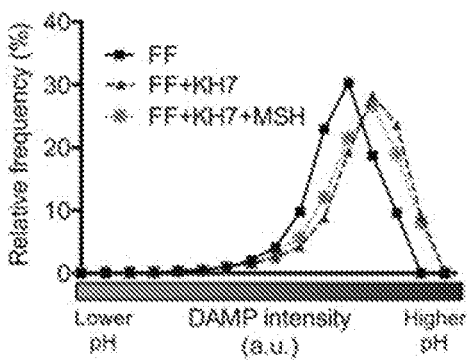
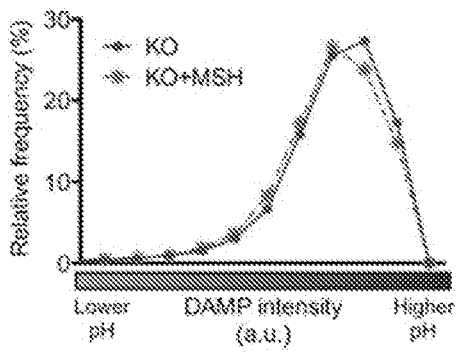
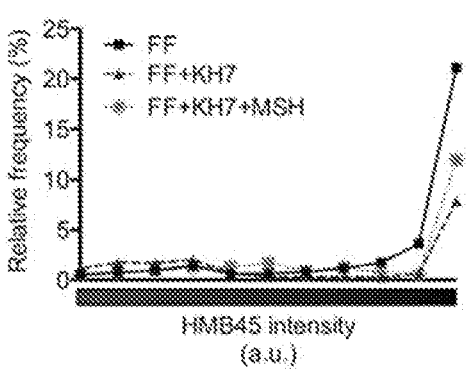
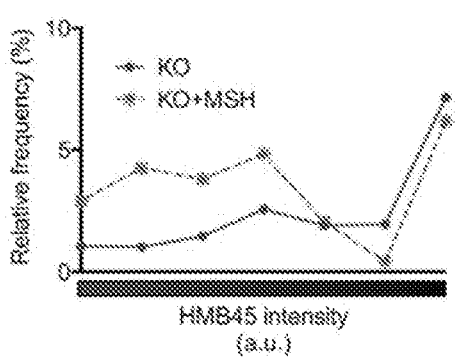
FIG. 8A
FIG. 8B
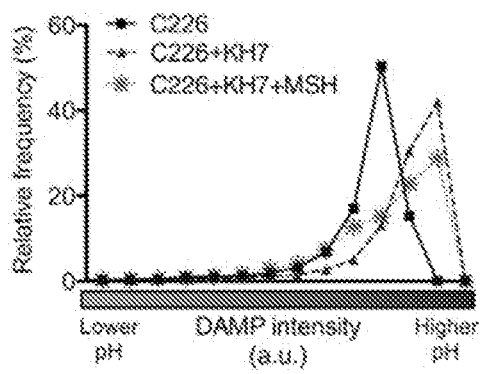
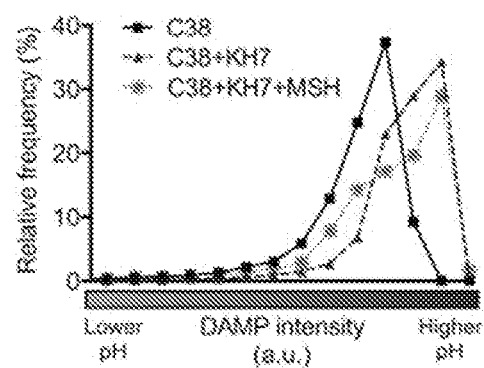
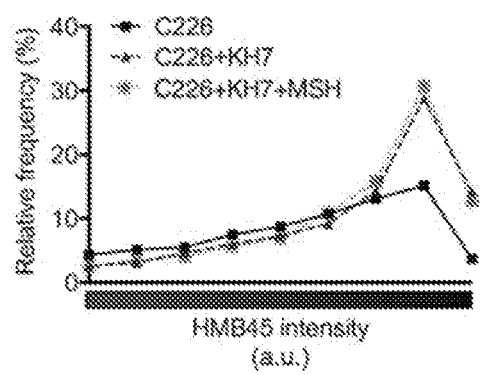
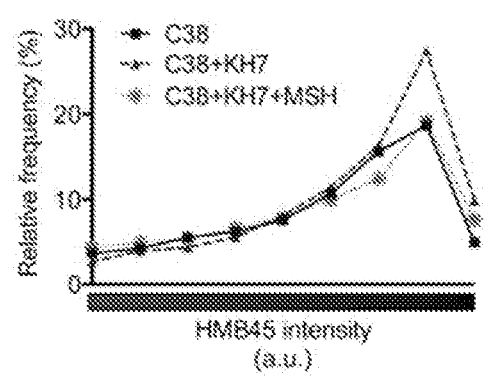
FIG. 8C
FIG. 8D

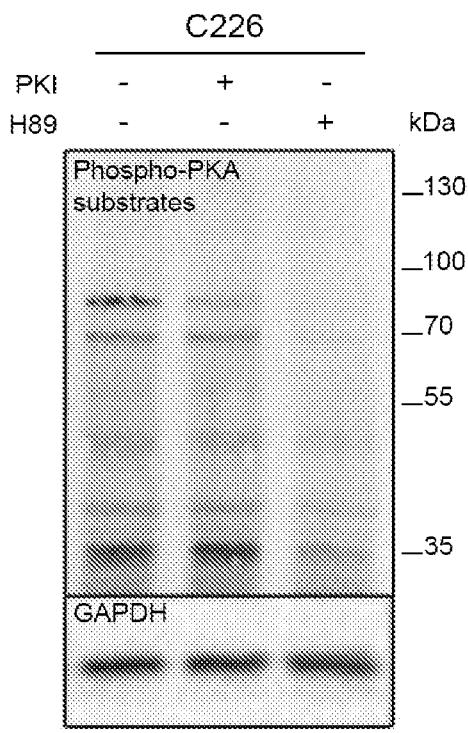 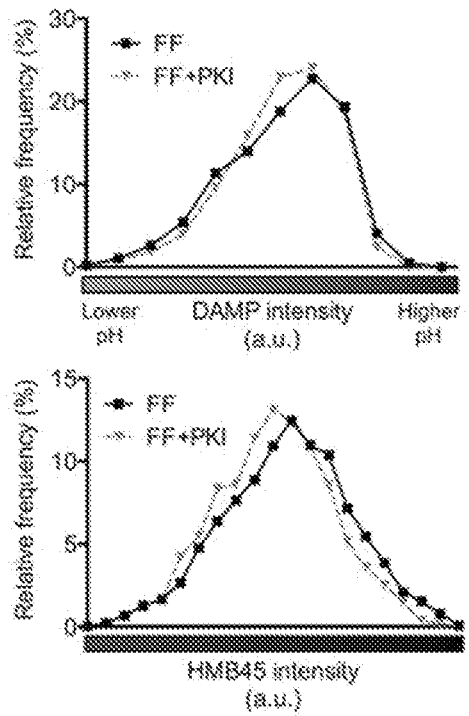
FIG. 10A    FIG. 10B
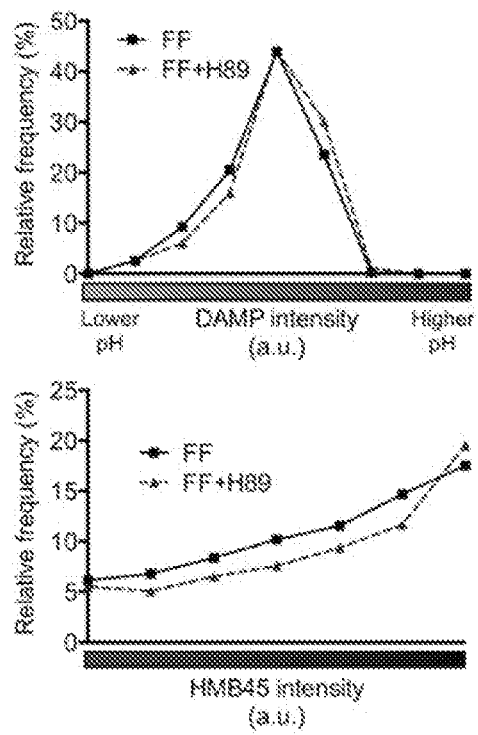 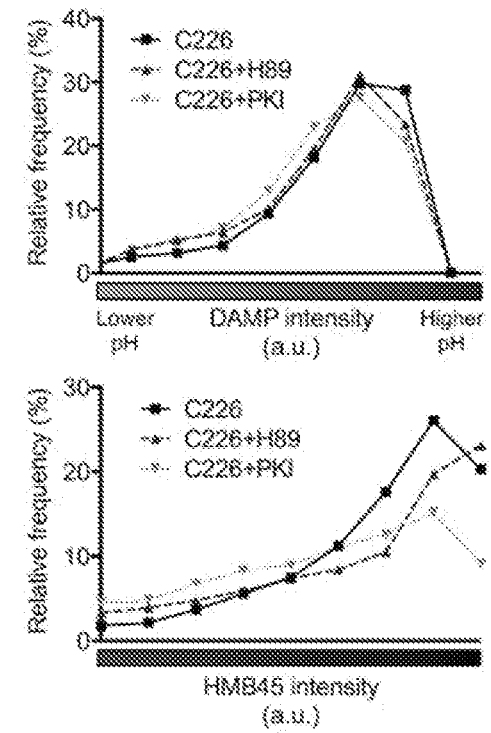
FIG. 10C    FIG. 10D

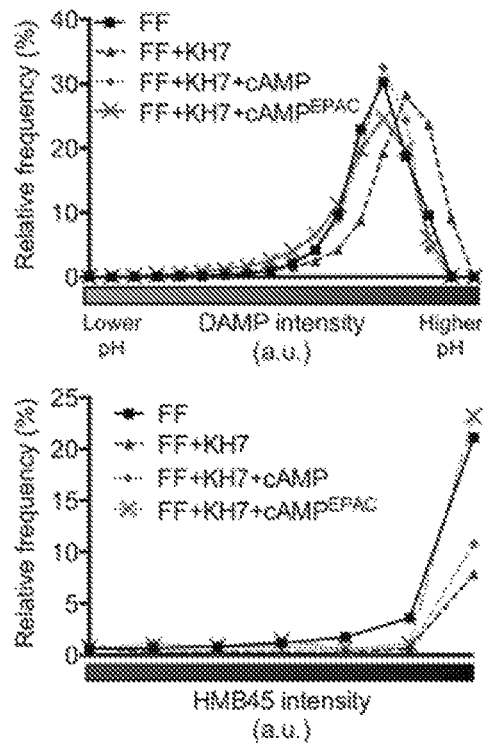
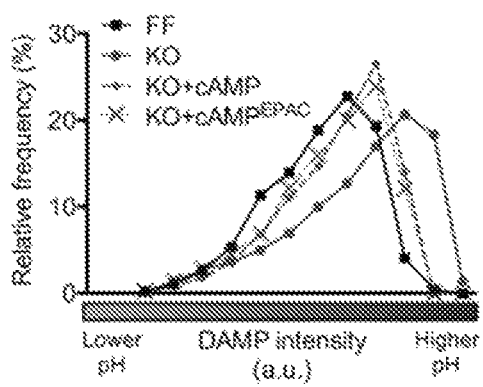
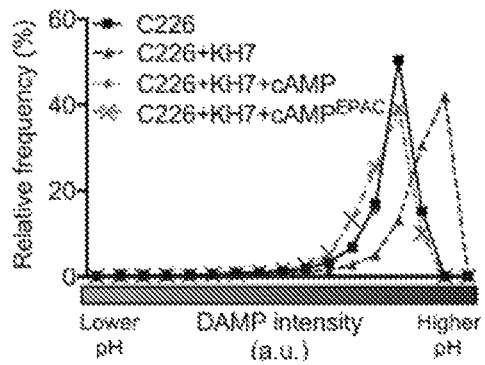
FIG. 12A  FIG. 12B
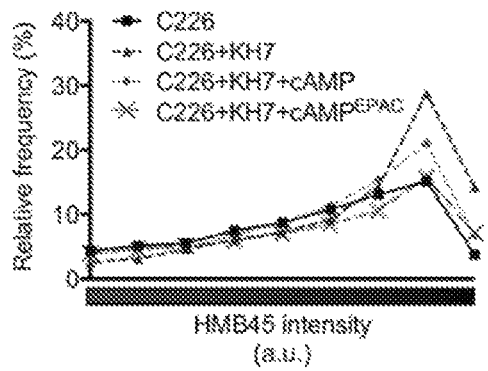
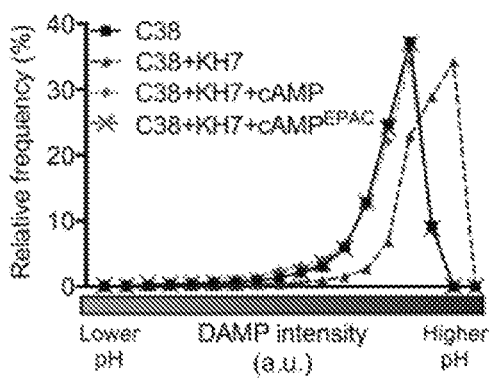
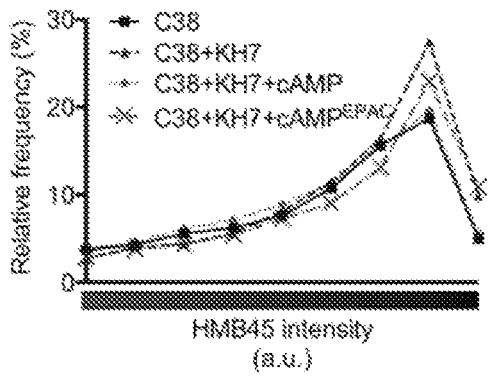
FIG. 12C  FIG. 12D

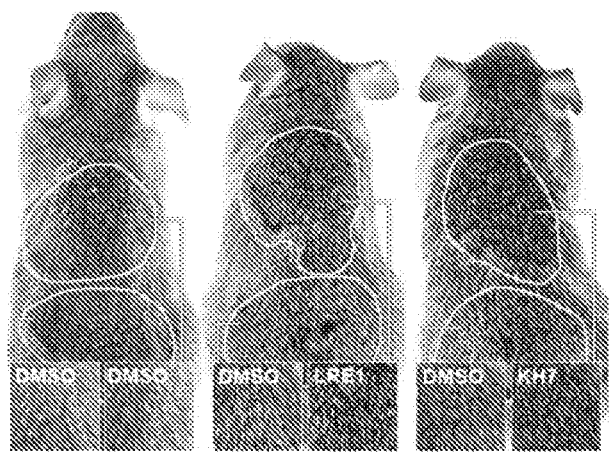
FIG. 16A
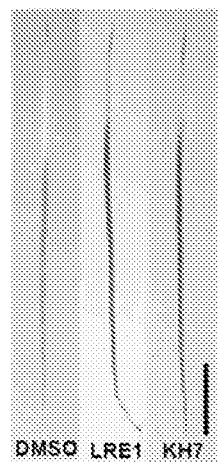 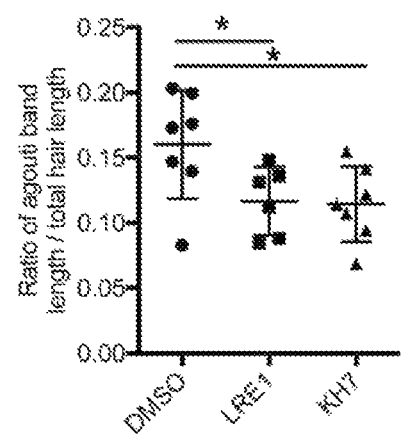
FIG. 16B  FIG. 16C
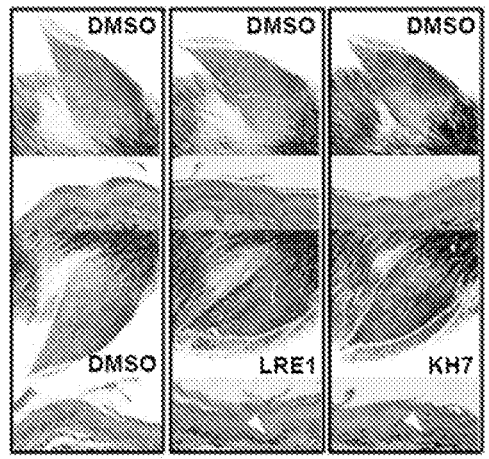
FIG. 16D

METHODS OF MODULATING MELANOSOME PH AND MELANIN LEVEL IN CELLS

CROSS-REFERENCE TO RELATED APPLICATIONS

This patent application is the U.S. national phase of International Application No. PCT/US2017/040428, which claims the benefit of U.S. Provisional Patent Application No. 62/357,606, filed Jul. 1, 2016, and U.S. Provisional Patent Application No. 62/480,189, filed Mar. 31, 2017, the entire contents of which are incorporated herein by reference.

STATEMENT REGARDING FEDERALLY SPONSORED RESEARCH AND DEVELOPMENT

This invention was made with Government support under Grant Number K08 CA 160657 awarded by the National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 886 Byte ASCII (Text) file named "741521_ST25.TXT" created on Dec. 28, 2018.

BACKGROUND OF THE INVENTION

Human pigmentation has psychosocial and cancer-risk significance; thus, understanding how baseline pigmentation is controlled has numerous clinical implications. Much of our current understanding of human pigmentation is based on the characterization of polymorphisms in genes important for pigmentation such as MC1R. Investigation of MC1R molecular polymorphisms have helped explain disorders of human pigmentation and the red-hair phenotype; however, signaling pathways that control pigmentation have remained elusive.

Melanin pigments are synthesized by melanocytes in highly specialized organelles called melanosomes. Melanosomal pH is an important regulator of melanogenesis and is implicated in tyrosinase activity, eumelanin/pheomelanin production ratio, as well as melanosome maturation. However, the mechanism by which melanocytes regulate melanosome pH remains poorly understood. Therefore, there is a need to identify new mechanisms by which melanocytes regulate melanosome pH and to identify new methods to regulate melanosome pH and human pigmentation. This invention provides such a mechanism and also provides new methods to regulate melanosome pH and human pigmentation.

BRIEF SUMMARY OF THE INVENTION

The invention provides a method of increasing the pH of a melanosome in a melanocyte comprising administering a therapeutically effective amount of a soluble adenylyl cyclase (sAC) inhibitor and/or an exchange protein activated by cyclic AMP (EPAC) inhibitor to the melanocyte. The invention also provides a method for increasing the amount of melanin in a melanocyte comprising administering a therapeutically effective amount of a sAC inhibitor and/or an EPAC inhibitor to the melanocyte.

The invention also provides a method for darkening the skin or hair pigmentation in a subject comprising administering a cosmetically effective amount of a sAC inhibitor and/or an EPAC inhibitor to the subject.

Additionally, the invention provides a method of treating a disease associated with decreased melanin in a subject comprising administering a therapeutically effective amount of a sAC inhibitor and/or an EPAC inhibitor to the subject.

The invention also provides a method of decreasing the pH of a melanosome in a melanocyte comprising administering a therapeutically effective amount of a soluble adenylyl cyclase (sAC) activator and/or an exchange protein activated by cyclic AMP (EPAC) activator to the melanocyte. The invention also provides a method for decreasing the amount of melanin in a melanocyte comprising administering a therapeutically effective amount of a sAC activator and/or an EPAC activator to the melanocyte.

The invention also provides a method for lightening the skin or hair pigmentation in a subject comprising administering a cosmetically effective amount of a sAC activator and/or an EPAC activator to the subject.

Additionally, the invention provides a method of treating a disease associated with increased melanin in a subject comprising administering a therapeutically effective amount of a sAC activator and/or an EPAC activator to the subject.

The invention also provides a method for preventing skin cancer in a subject with increased susceptibility to skin cancer comprising administering a prophylactically effective amount of a sAC inhibitor and/or an EPAC inhibitor to the subject.

Additionally, the invention provides a composition comprising a sAC inhibitor and/or an EPAC inhibitor or a sAC activator and/or and EPAC activator and a cosmetically acceptable carrier.

BRIEF DESCRIPTION OF THE SEVERAL VIEWS OF THE DRAWING(S)

Figure 1B:
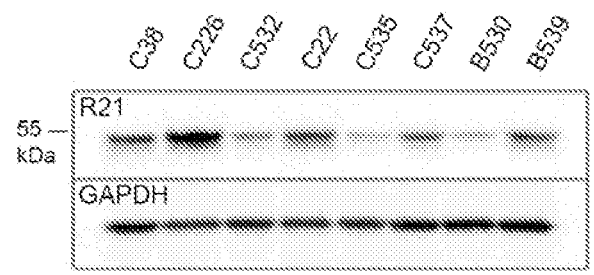
Figure 1C:
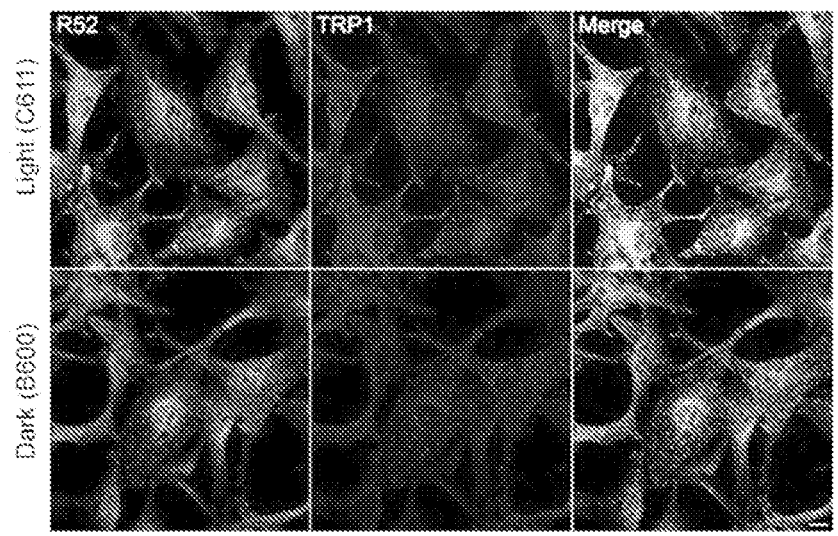
Figure 1D:
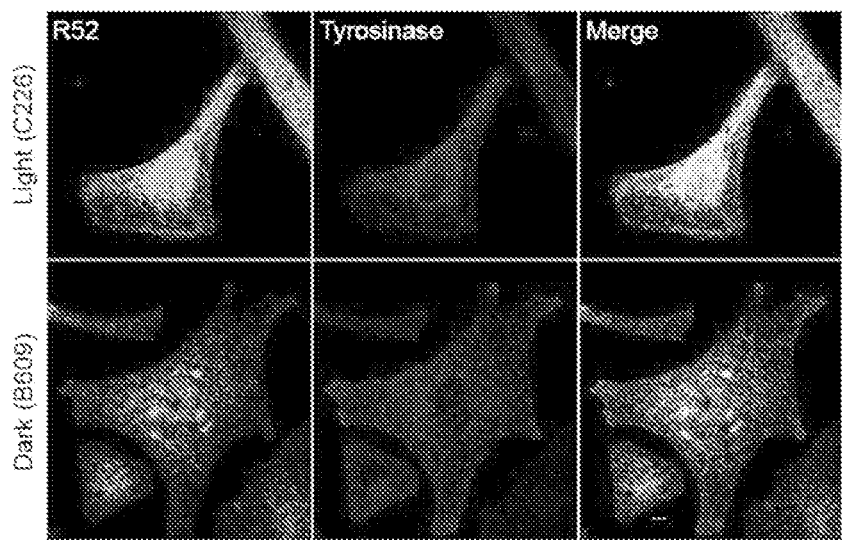
Figure 1E:
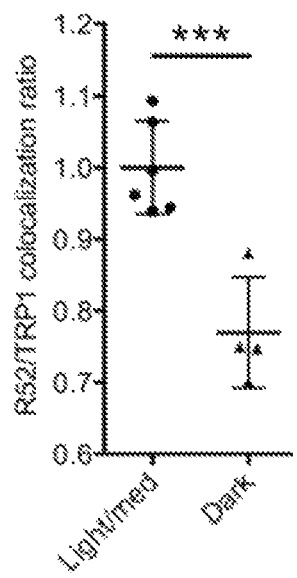
Figure 1F:
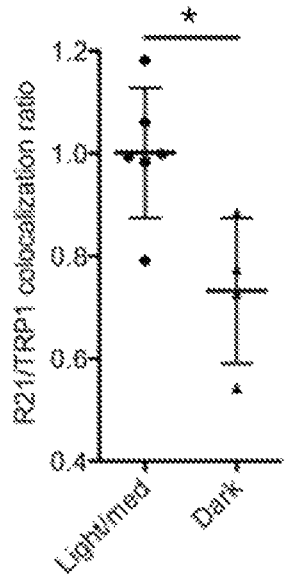
Figure 1G:
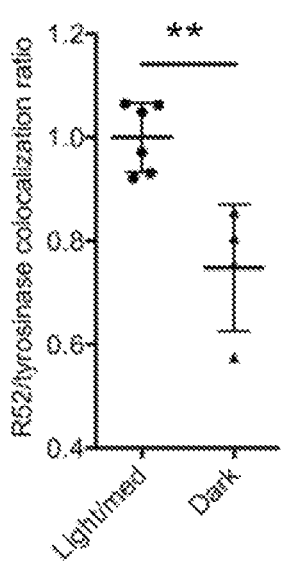
Figure 1H:
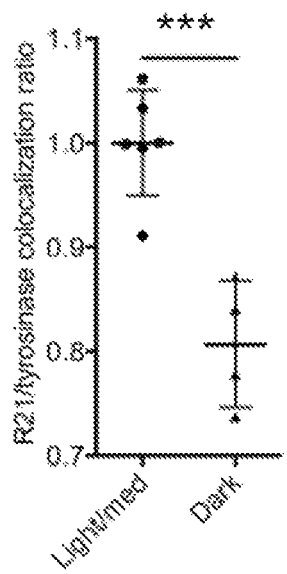

FIGS. 1A-1H are results from experiments analyzing soluble adenylyl cyclase (sAC) expression in human melanocytes. FIG. 1A is an image of RT-PCR results of "light" and "dark" human melanocytes (n=2 per cell line). FIG. 1B is a Western blot image analyzing sAC expression using the mouse monoclonal R21 sAC antibody in multiple light/med (C38, C226, C532, C22, C535, and C537) and dark (B530 and B539) human melanocyte cell lines. FIGS. 1C and 1D are confocal images of light (upper panels) and dark (lower panels) melanocytes stained with the sAC specific antibody R52, a TRP1 antibody, or a tyrosinase antibody. FIGS. 1E and 1F are graphs calculating the ratio of colocalization between sAC and TRP1 positive organelles in light and medium melanocytes relative to dark melanocytes. FIGS. 1G and 1H are graphs calculating the ratio of colocalization between sAC (R52, R21) and tyrosinase positive organelles in light and medium melanocytes relative to dark melanocytes. For FIGS. 1E-1H data are representative of an experiment (n=10 per cell line, Light/med cell lines=6, Dark cell lines=4, distinct human cell lines). Comparison of sAC colocalization at melanosomes in "light/medium" versus "dark" melanocytes normalized to "Light/medium" cells. Comparison performed 2 times in duplicate. Students I-test, *P<0.05, P<0.01, *P<0.001. Scale bar, 10 μm.

Figure 2A:
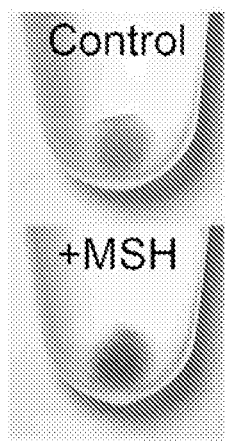
Figure 2B:
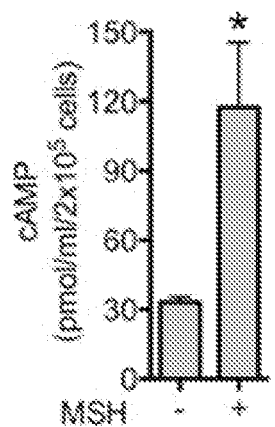
Figure 2C:
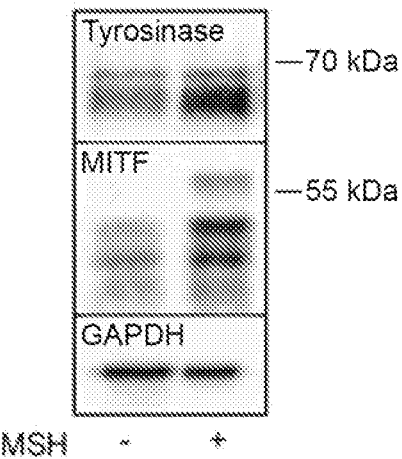
Figure 2D:
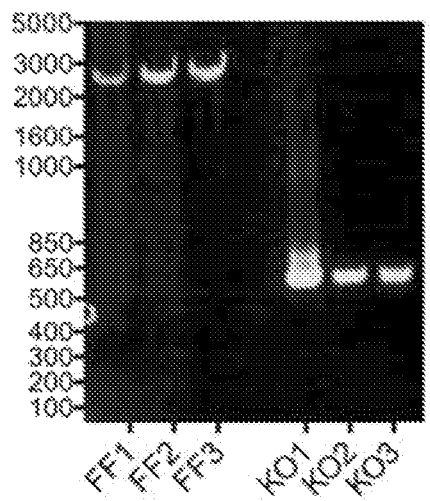
Figure 2E:
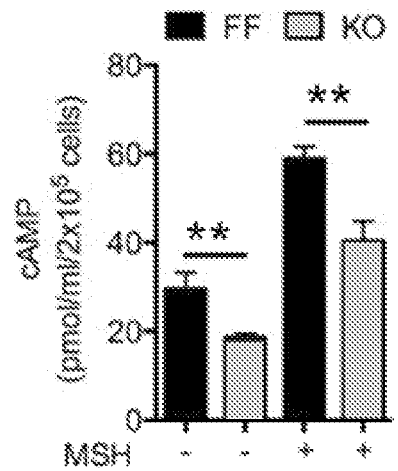
Figure 2F:
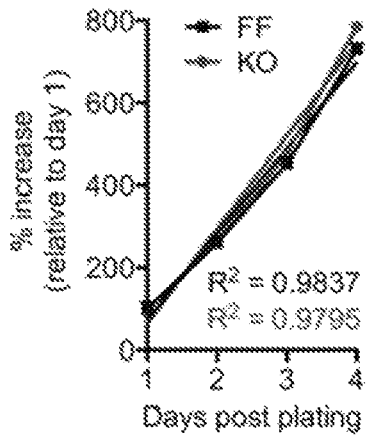
Figure 2G:
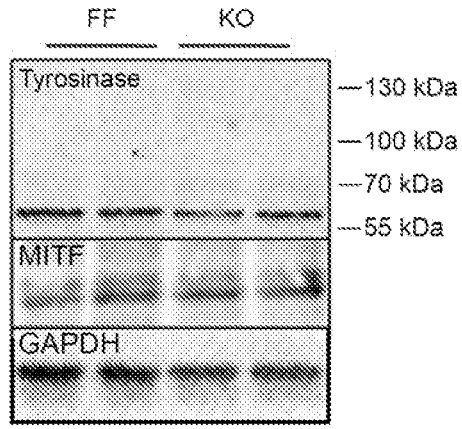

FIGS. 2A-2G are results from experiments establishing the ADCY10$^{-/-}$ (sAC$^{KO}$) mouse melanocyte cell lines. FIG. 2A are images of cell pellets of immortalized ADCY10$^{fl/fl}$ mouse melanocytes grown in the absence or presence of 100 nM melanocyte-stimulating hormone (MSH) for 72 hours. FIG. 2B is a graph depicting the cAMP accumulation in ADCY10$^{fl/fl}$ mouse melanocytes in the absence (−) or presence (+) of 100 nM MSH. FIG. 2C is an image of a Western blot showing the expression level of tyrosinase and MITF in ADCY10$^{fl/fl}$ mouse melanocytes in the absence (−) or presence (+) of 100 nM MSH. FIG. 2D is an image of RT-PCR results confirming the presence (KO1-3) or absence (FF1-3) of ADCY10 exon deletion in three distinct sets of immortalized ADCY10$^{fl/fl}$ mouse melanocytes. FIG. 2E is a graph depicting the cAMP accumulation in sAC$^{FF}$ and sAC$^{KO}$ mouse melanocytes in the absence (−) or presence (+) of 100 nM MSH. FIG. 2F is a graph depicting the cell proliferation of sAC$^{FF}$ and sAC$^{KO}$ mouse melanocytes over 4 days. FIG. 2G is an image of a Western blot showing the expression level of tyrosinase and MITF in sAC$^{FF}$ (FF) or sAC$^{KO}$ (KO) mouse melanocytes. Duplicate samples examined. Students t-test, *P<0.05, **P<0.01.

Figure 3A:
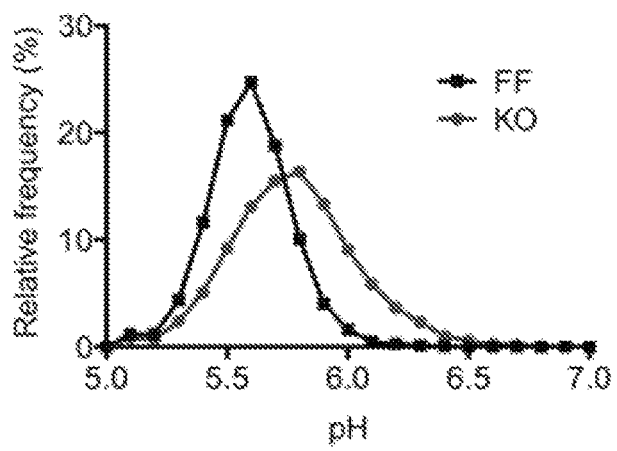
Figure 3B:
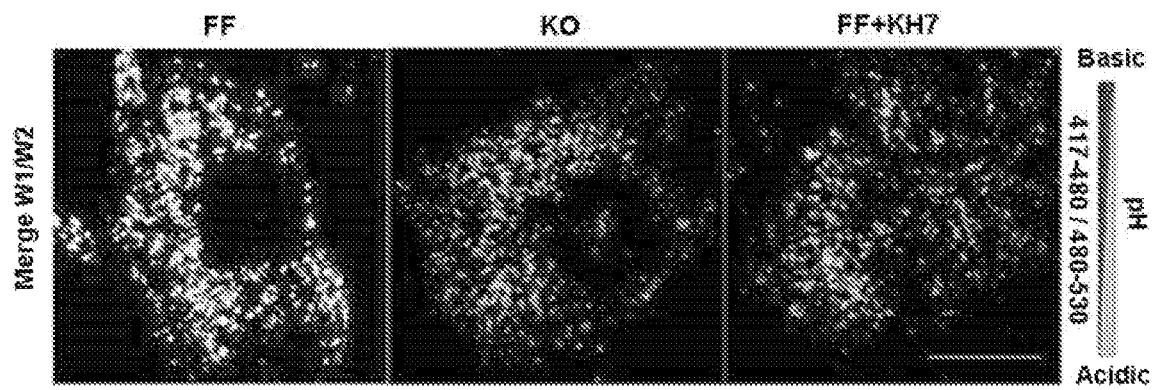
Figure 3C:
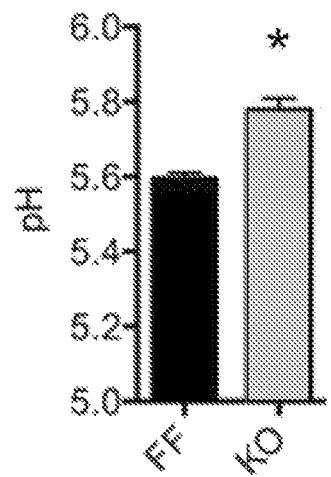

FIGS. 3A-3C are results from experiments analyzing the pH of the sAC$^{FF}$ and sAC$^{KO}$ mouse melanocytes. FIG. 3A is a graph depicting the frequency distribution of emission ratio of W1 (417-480 nm)/W2 (490-530 nm) at 405 nm excitation of LysoSensor-visualized organelles in sAC$^{FF}$ (FF) and sAC$^{KO}$ (KO) melanocytes. FIG. 3B is confocal microscope images of sAC$^{FF}$ (FF, left panel), sAC$^{KO}$ (KO, middle panel), and KH7-treated sAC$^{FF}$ (FF+KH7, right panel) mouse melanocytes following incubation with LysoSensor. Right side of figures is the color scale used for LysoSensor. FIG. 3C is a graph of the predicted average pH values as determined from a LysoSensor calibration curve, sAC$^{FF}$ (FF) and sAC$^{KO}$ (KO) *P<0.05.

FIGS. 4A-4E are the results for DAMP experiments to analyze the pH of melanosomes in the sAC$^{FF}$ and sAC$^{KO}$ mouse melanocytes. FIG. 4A is a graph illustrating the percent of DAMP positive organelles reaching or exceeding the lower DAMP fluorescence intensity threshold set for sAC$^{FF}$ mouse melanocytes (FF) in sAC$^{KO}$ mouse melanocytes (KO), sAC$^{FF}$ mouse melanocytes following 4 hours of KH7 (30 μM, FF+KH7) or sAC$^{KO}$ mouse melanocytes following 4 hours of KH7 (30 μM, KO+KH7). FIG. 4B is a graph illustrating the percent of DAMP+ organelles identified as melanosomes by co-staining with HMB45 in sAC$^{FF}$ (FF) and sAC$^{KO}$ (KO) mouse melanocytes treated with vehicle or KH7 (30 μM (FF+KH7) or (KO+KH7)) for 4 hours. FIGS. 4A and 4B are representative figures of an experiment (number of melanosomes analyzed: FF=1905, n=30, KO=2178, n=30, FF+KH7=1560, n=30, KO+KH7=1915, n=30) performed 8 times in duplicate. FIG. 4C is a graph illustrating the number of HMB45 positive melanosomes per unit cell area in sAC$^{FF}$ (FF) and sAC$^{KO}$ (KO) mouse melanocytes. This is a representative figure of an experiment performed in duplicate (n=10 per cell line). FIG. 4D is confocal microscopic images of DAMP (green) and HMB45 (red) immunofluorescence in sAC$^{FF}$ (FF), sAC$^{KO}$ (KO) and cAMP-treated sAC$^{KO}$ (KO+cAMP) melanocytes. Scale bar, 10 μm. FIG. 4E are graphs illustrating the frequency distribution of DAMP fluorescence intensity at HMB45 positive melanosomes (upper panel) and the frequency distribution of HMB45 fluorescence intensity (lower panel) in sAC$^{FF}$ (FF), sAC$^{KO}$ (KO), and KH7-treated sAC$^{FF}$ (FF+KH7) mouse melanocytes.

FIGS. 5A-5D are results of experiment analyzing the effect of pharmacologic inhibition of sAC on melanosome pH. FIG. 5A is a graph depicting the frequency distribution of emission ratio of W1 (417-480 nm)/W2 (490-530 nm) at 405 nm excitation of LysoSensor-visualized organelles of sAC$^{FF}$ (FF) cells in the absence (FF) or presence of 30 μM KH7 (FF+KH7) or LRE1 (FF+LRE1). FIG. 5B is a graph of the predicted average pH values as determined from a LysoSensor calibration curve of KH7 (FF+KH7) or LRE1 (FF+LRE1) treated sAC$^{FF}$ mouse melanocytes, **P<0.01. FIG. 5C is a graph illustrating the frequency distribution of emission ratio of W1 (417-480 nm)/W2 (490-530 nm) at 405 nm excitation of LysoSensor visualized organelles (top panel) and average pH values (bottom panel) as determined from a LysoSensor calibration curve in DMSO-treated (KO), KH7-treated (KO+KH7), and LRE1-treated (KO+LRE1) sAC$^{KO}$ mouse melanocytes. FIG. 5D is a graph illustrating the DAMP fluorescence at HMB45 positive melanosomes (left) and HMB45 fluorescence (right) in sAC$^{FF}$ (FF) or sAC$^{KO}$ melanocytes after incubation with DMSO (KO) or 30 μM KH7 (KO+KH 7). FIGS. 5C and 5D are representative of experiments analyzing ≥1500 melanosomes (n≥30) per condition performed at least 2 times in duplicate.

Figure 6A:
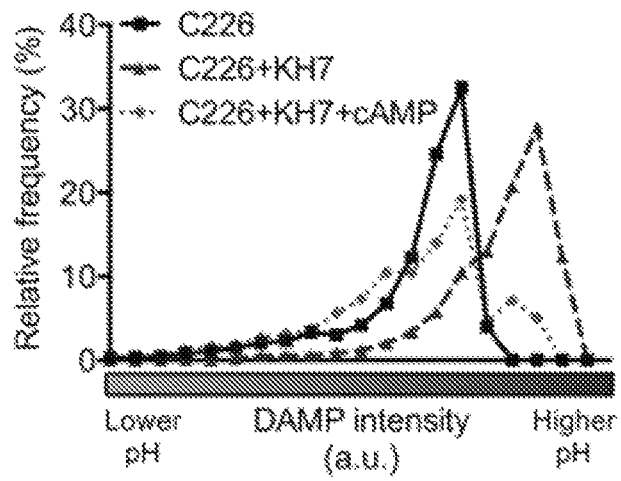
Figure 6B:
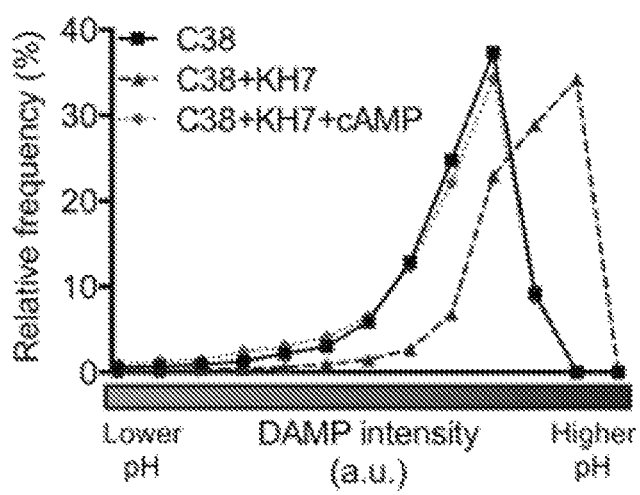

FIGS. 6A and 6B are results of experiments analyzing the effect of pharmacologic inhibition of sAC on melanosome pH in human melanocytes. FIGS. 6A and 6B provide graphs illustrating the frequency distribution of DAMP fluorescence intensity at HMB45 positive melanosomes in C226 (FIG. 6A) and C38 (FIG. 6B) human melanocytes following treatment with vehicle control, KH7, or KH7+cAMP.

FIGS. 7A-7D provide results from experiments analyzing the effect of increased cAMP on melanosome pH. FIG. 7A is a graph illustrating the frequency distribution of DAMP fluorescence intensity at HMB45 positive melanosomes in sAC$^{FF}$ (FF), sAC$^{KO}$ (KO), and cAMP-treated sAC$^{KO}$ (KO+cAMP) mouse melanocytes. FIG. 7B is a graph illustrating DAMP (top panel) and HMB45 (bottom panel) fluorescence of sAC$^{FF}$ mouse melanocytes following incubation with the nonselective cAMP [Sp-8-CPT-cAMPs] (FF+cAMP, 500 μM), EPAC-selective cAMP [8-pHPT-2'-O-Me-cAMP] (FF+cAMPEPAc) or vehicle control (FF) for 4 hours. This is a representative figure of an experiment (number of melanosomes analyzed: FF=2286, n=30, FF+cAMP=2987, n=30, FF+cAMPEPAc=2723, n=30) performed 3 times in duplicate. FIG. 7C is a graph illustrating the frequency distribution of DAMP fluorescence intensity at HMB45 positive melanosomes in sAC$^{FF}$ (FF), KH7-treated sAC$^{FF}$ (FF+KH7), and KH7+cAMP-treated sAC$^{FF}$ (FF+KH7+cAMP) mouse melanocytes. FIG. 7D is a graph illustrating DAMP (top panel) and HMB45 (bottom panel) fluorescence of human melanocytes following incubation with (C226+cAMP) or without (C226) 500 μM cAMP [Sp-8-CPT-cAMPs] for 4 hours. This is a representative figure of an experiment (number of melanosomes analyzed: C226=3014, n=30, C226+cAMP=1040, n=30).

FIGS. 8A-8D provide results from experiments showing that MSH does not rescue altered melanosomal pH due to loss of sAC function. FIG. 8A is a graph illustrating DAMP fluorescence (top panel) and HMB45 fluorescence (bottom panel) profile in sAC$^{FF}$ mouse metanocytes following 4-hour incubation with vehicle (FF), KH7 (30 μM, FF+KH7), or KH7+100 nM MSH (FF+KH7+MSH). This is a representative figure of an experiment (number of melanosomes analyzed: FF=1666, n=30, FF+KH7=1928, FF+MSH+KH7=2043 n=30) performed 2 times in duplicate. FIG. 8B is a graph illustrating DAMP fluorescence (top panel) and HMB45 fluorescence (bottom panel) profile of sAC$^{KO}$ mouse melanocytes following incubation with vehicle (KO) or 100 nM MSH (KO+MSH) for 4 hours. FIGS. 8C and 8D are graphs illustrating DAMP fluorescence (top panel) and HMB45 fluorescence (bottom panel) profile of human melanocytes (FIG. 8C=C226 and FIG. 8D=C38) following 4-hour treatment with 30 μM KH7 (+KH7) or KH7+100 nM MSH (+KH7+MSH). This is a representative figure of an experiment (number of melanosomes analyzed: C226=5365, n=30, C226+KH7=4730, n=30, C226+MSH+ KH7=6123, n=30, C38=4373, n=30, C38+KH7=3261, n=30, C38+MSH+KH7=3987, n=30) performed 2 times in duplicate.

Figure 9A:
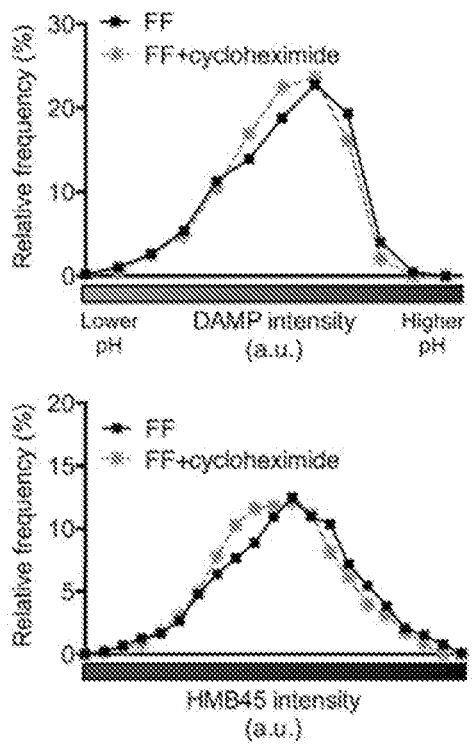
Figure 9B:
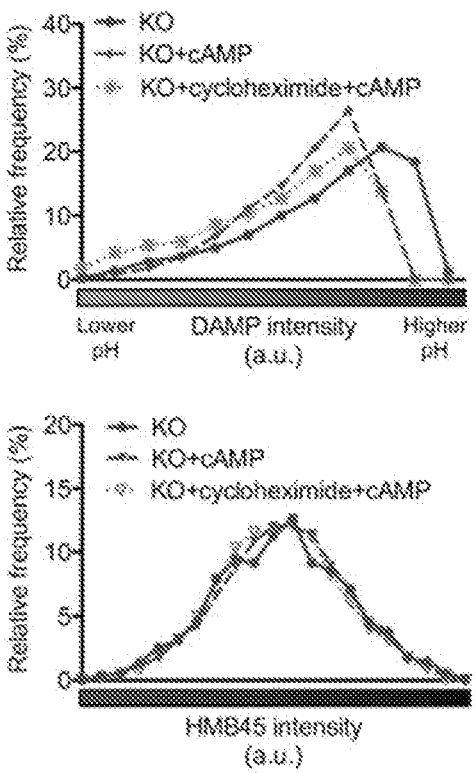

FIGS. 9A-9B are results from experiments analyzing the effect of cycloheximide on melanosome pH. FIG. 9A are graphs illustrating DAMP (top panel) and HMB45 (bottom panel) fluorescence of sAC$^{FF}$ mouse melanocytes following incubation with or without cycloheximide (10 μM) for 4 hours. This is a representative figure of an experiment (number of melanosomes analyzed: FF=2286, n=30. FF+cycloheximide=2058, n=30). FIG. 9B are graphs illustrating DAMP (top panel) and HMB45 (bottom panel) fluorescence in sAC$^{KO}$ mouse melanocytes following incubation with vehicle control (KO), cAMP [Sp-8-CPT-cAMPs] alone (KO+cAMP), or cAMP+10 μM cycloheximide (KO+cyclohexamide+cAMP) for 4 hours. This is a representative figure of an experiment (number of melanosomes analyzed: KO=2251, n=30. KO+cAMP=2723, n=30, KO+cycloheximide+cAMP=1709, n=30).

Figure 10E:
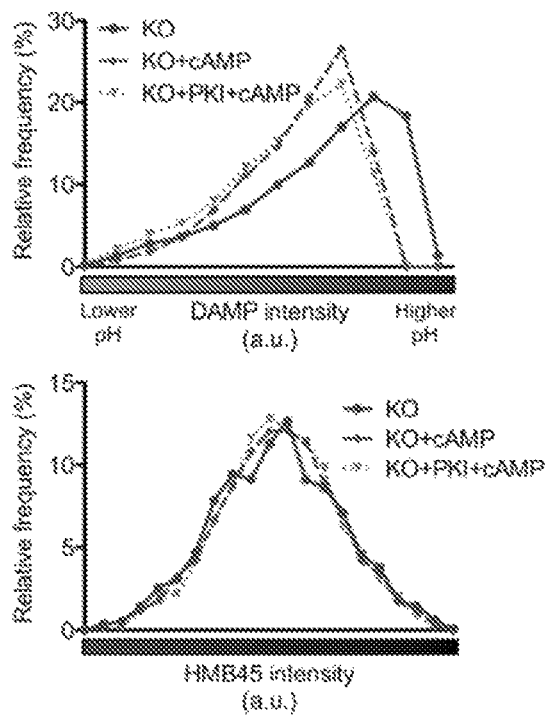
Figure 10F:
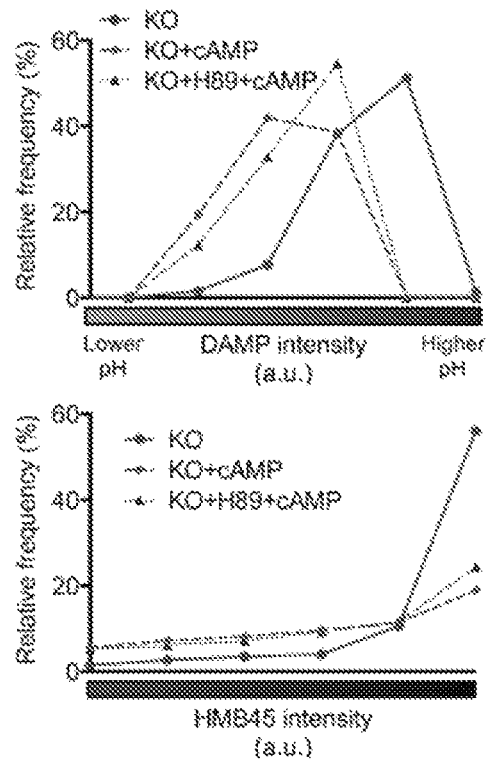

FIGS. 10A-10F are results of experiments analyzing the effect of PKA on melanosomal pH. FIG. 10A is a Western blot image illustrating the PKA substrate phosphorylation pattern of human melanocytes following incubation for 4 hours in DMSO (−), PKI, or H89. FIG. 10B are graphs illustrating DAMP (upper panel) and HMB45 (lower panel) fluorescence of sAC$^{FF}$ mouse melanocytes following incubation with vehicle (FF) or PKI (10 μM, FF+PKI) for 4 hours. This is a representative figure of an experiment (number of melanosomes analyzed: FF=2286, n=30, FF+PKI=1928, n=30). FIG. 10C are graphs illustrating DAMP (upper panel) or HMB45 (lower panel) fluorescence of sAC$^{FF}$ mouse melanocytes following incubation with vehicle (FF) or H89 (FF+H89, 10 μM) for 4 hours. This is a representative figure of an experiment (number of melanosomes analyzed: FF=5533, n=30, FF+H89=3454, n=30). FIG. 10D are graphs illustrating DAMP fluorescence (upper panel) and HMB45 fluorescence (lower panel) profiles in human melanocytes (C226) following incubation for 4 hours in either H89 (C226+H89, 10 μM) or PKI (C226+PKI). This is a representative figure of an experiment (number of melanosomes analyzed: C226=2530, n=30, C226+ H89=6251, n=30, C226+PKI=7067, n=30). FIG. 10E is a graph illustrating DAMP fluorescence (upper panel) and HMB45 fluorescence profile (lower panel) in sAC$^{Ko}$ mouse melanocytes following incubation in vehicle control (KO), cAMP [Sp-8-CPT-cAMPs] (KO+cAMP) or cAMP+10 μM PKI (KO+cAMP+PKI) for 4 hours. This is a representative figure of an experiment (number of melanosomes analyzed: KO=2251, n=30, KO+cAMP=2723, n=30, KO+PKI+ cAMP=2253, n=30). FIG. 10F are graphs illustrating DAMP fluorescence (upper panel) and HMB45 fluorescence profile (lower panel) in sAC$^{KO}$ mouse melanocytes following incubation in vehicle control (KO), cAMP [Sp-8-CPT-cAMPs] (KO+cAMP) or cAMP+10 μM H89 (KO+cAMP+H89) for 4 hours. This is a representative figure of an experiment (number of melanosomes analyzed: KO=9157, n=30, KO+cAMP=3800, n=30, KO+H89+cAMP=3523, n=30).

Figure 11A:
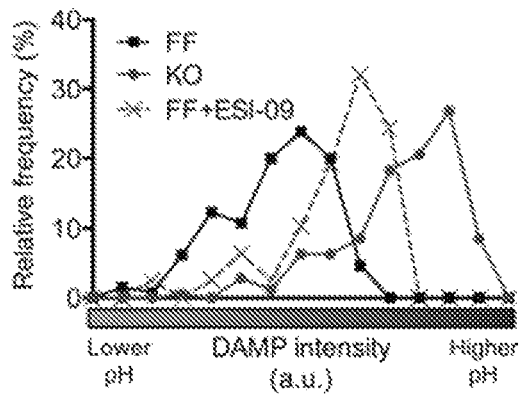
Figure 11B:
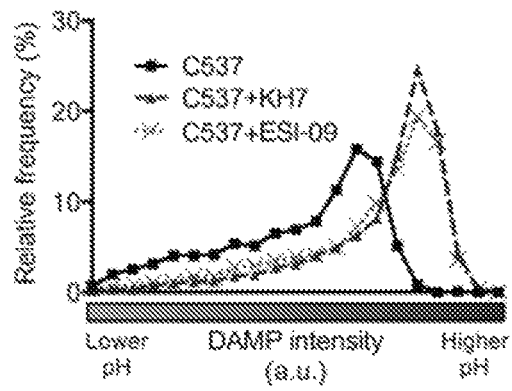
Figure 11C:
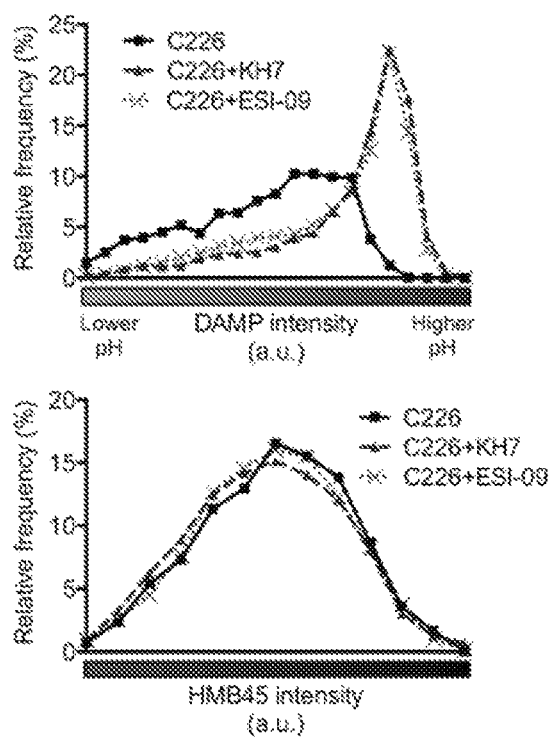
Figure 11D:
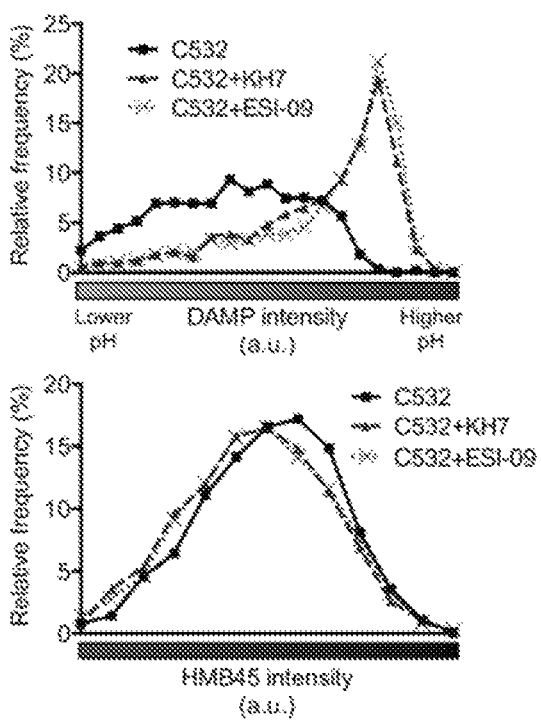
Figure 11E:
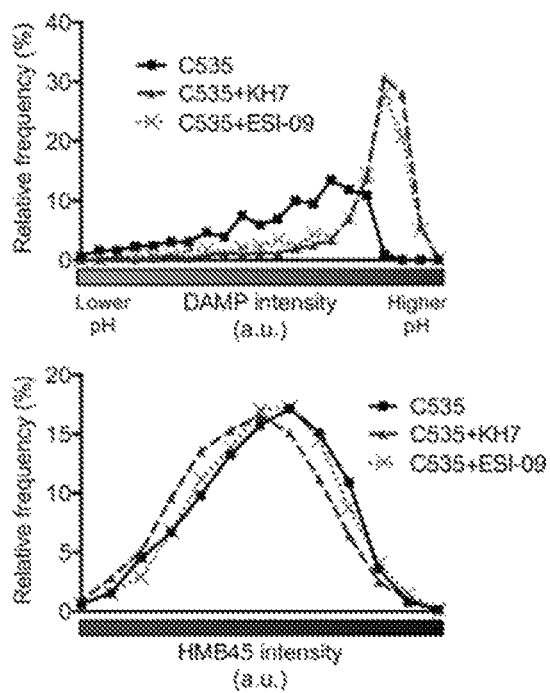
Figure 11F:
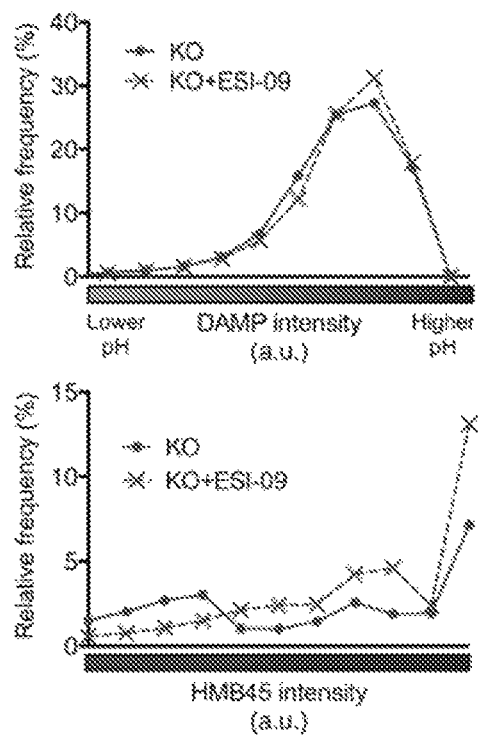

FIGS. 11A-11F are results from experiments showing that inhibition of EPAC increases melanosomal pH. FIG. 11A is a graph illustrating frequency distribution of DAMP fluorescence intensity at HMB45 positive melanosomes in sAC$^{FF}$ (FF), sAC$^{KO}$ (KO), and ESI-09-treated sAC$^{FF}$ (FF+ ESI-09) mouse melanocytes. FIG. 11B is a graph illustrating the frequency distribution of DAMP fluorescence intensity at HMB45 positive melanosomes in human melanocytes following treatment with vehicle control (C537), KH7 (C537+KH7, or ESl-09 (C537+ESl-09). FIGS. 11C-11E are graphs illustrating DAMP fluorescence (upper panel) and HMB45 fluorescence profile (lower panel) of various strains of human melanocytes following incubation in vehicle control, KH7 (+KH7) or ESl-09 (+ESl-09) for 4 hours. Number of melanosomes analyzed: C226=1617, n=30, C226+ KH7=1541, n=30, C226+ESl-09=2407, n=30, C532=1037, n=30, C532+KH7=1366, n=30, C532+ESl-09=1838, n=30, C535=624, n=30, C535+KH7=2502, n=30, C535+ESl-09=1189, n=30, C537=1303, n=30, C537+KH7=3148, n=30, C537+ESl-09=1677, n=30. FIG. 11F are graphs illustrating DAMP fluorescence (upper panel) and HMB45 fluorescence profile (lower panel) of sAC$^{KO}$ mouse melanocytes following treatment with vehicle control (KO) or ESl-09. Number of melanosomes analyzed: KO=2289, n=30, KO+ESl-09=2177, n=30.

FIGS. 12A-12D are results from experiments showing that activation of EPAC decreases melanosomal pH. FIG. 12A is a graph illustrating the frequency distribution of DAMP fluorescence intensity at HMB45 positive melanosomes in sAC$^{FF}$ (FF), and sAC$^{KO}$ melanocytes in absence (KO) or presence of nonselective-cAMP analog (KO+cAMP or EPAC-selective-cAMP analog (KO+cAMP EPAC). FIG. 12B are graphs illustrating DAMP fluorescence (upper panel) and HMB45 fluorescence profile (lower panel) of sAC$^{FF}$ mouse melanocytes following 4-hour treatment with vehicle (FF), KH7 alone (FF+KH7), KH7+500 μM nonselective cAMP [Sp-8-CPT-cAMPs] (FF+KH7+cAMP), or KH7+500 μM EPAC-selective cAMP [8-pHPT-2'-O-Me-cAMP] (FF+KH7+cAMP EPAC). Number of melanosomes analyzed: FF=5533, n=30, FF+KH7=6533, n=30, FF+KH7+ cAMP=2873, n=30, FF+KH7+cAMP EPAC=3564, n=30. FIGS. 12C and 12D are graphs illustrating DAMP fluorescence (upper panel) and HMB45 fluorescence profile (lower panel) in human melanocytes (C226 and C38) following 4-hour treatment with vehicle, KH7 alone (+KH7), KH7+ 500 μM nonselective cAMP [Sp-8-CPT-cAMPs] (+KH7+ cAMP), or KH7+500 μM EPAC-selective cAMP [8-pHPT-2'-O-Me-cAMP] (+KH7+cAMP EPAC). C226=5365, n=30, C226+KH7=4730, n=30, C226+KH7+cAMP=6333, n=30, C226+KH7+cAMP=4335, n=30, C38=4373, n=30, C38+ KH7=3261, n=30, C38+KH7+cAMP=3484, n=30, C38+ KH7+cAMP EPAC=5568, n=30.

Figure 13A:
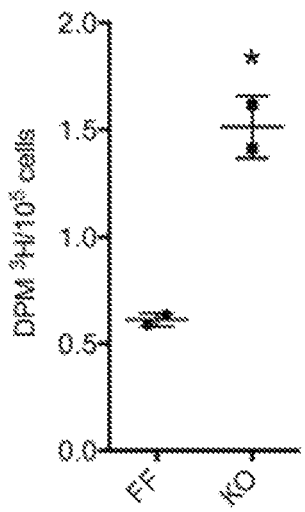
Figure 13B:
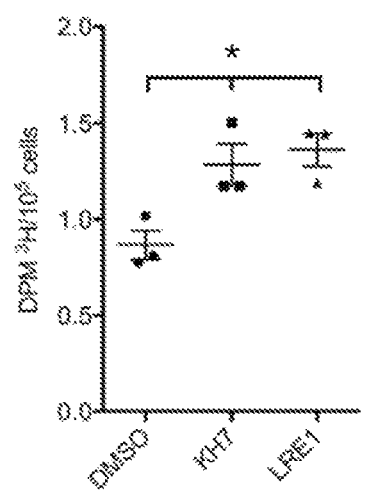
Figure 13C:
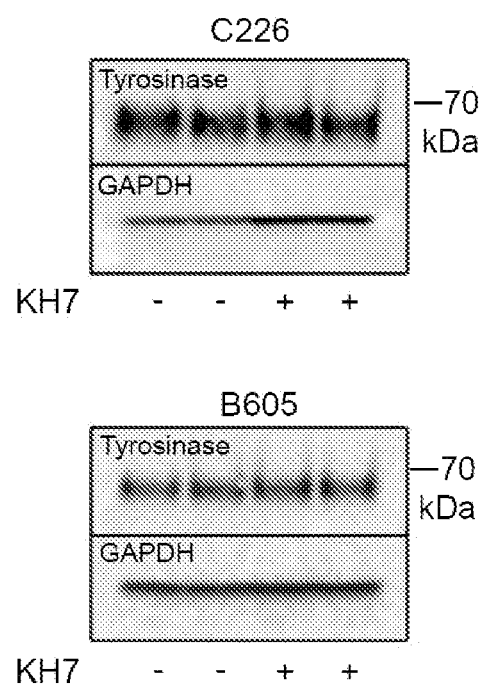

FIG. 13A-13C are results from experiments analyzing the effect of sAC on tyrosinase activity. FIG. 13A is a graph illustrating the in vivo tyrosinase activity of sAC$^{FF}$ (FF) and sAC$^{KO}$ (KO) mouse melanocytes as measured by $^3H_2O$ production per cell (n=2, each point is the average of duplicate determinations). FIG. 13B is a graph illustrating the in vivo tyrosinase activity of human melanocytes treated with KH7 (30 μM), LRE1 (50 μM) or vehicle for 8 hours as measured by $^3H_2O$ production per cell (n=3 distinct human cell lines, each point is the average of duplicate determinations). FIG. 13C are images of Western blots analyzing human melanocytes (C226 upper panel and 8605 lower panel) for tyrosinase expression following incubation in DMSO or KH7 (30 μM) for two days. *P<0.05.

Figure 14A:
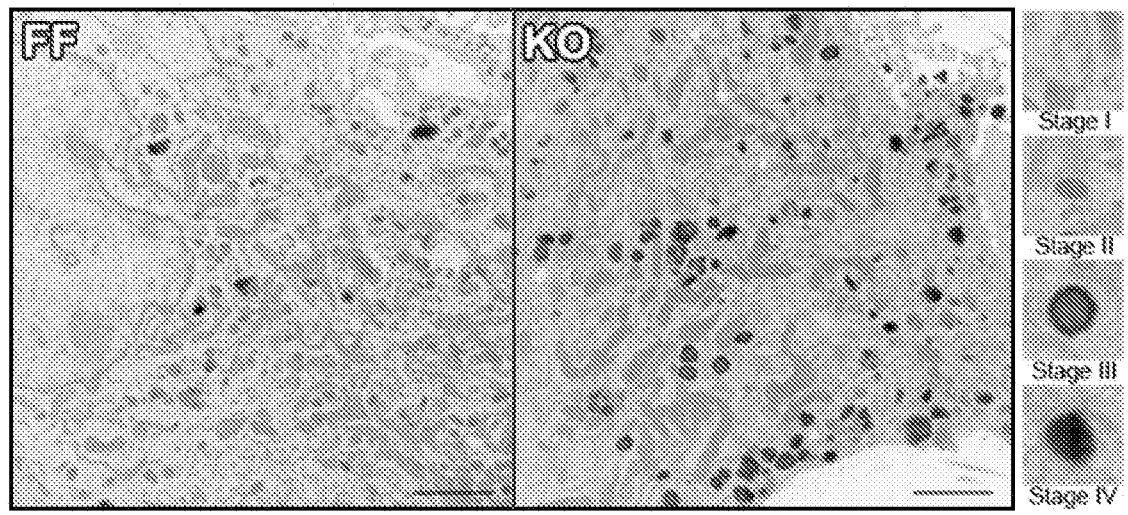
Figure 14B:
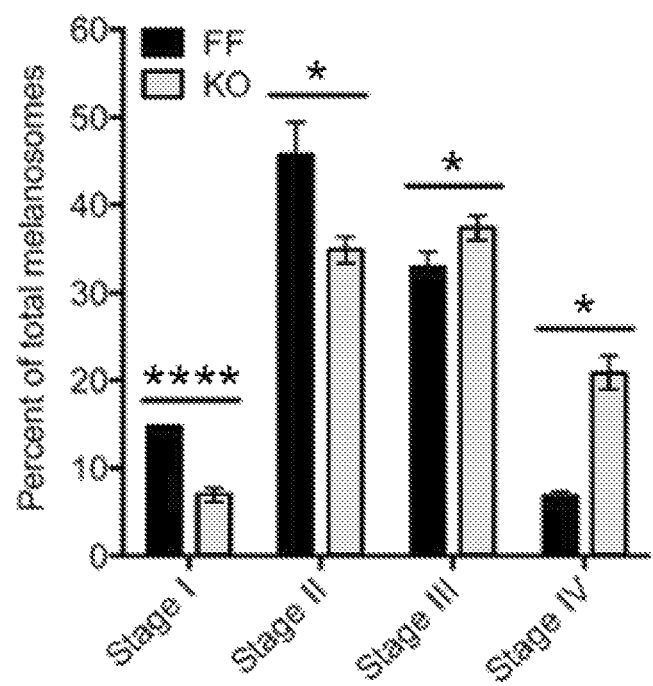

FIGS. 14A-14D are results from experiments analyzing the effect of sAC on melanogenesis. FIG. 14A is the electron microscopic evaluation of the melanosome morphology of sAC$^{FF}$ and sAC$^{KO}$ mouse melanocytes (panel on right provides examples of melanosomes at different stages. FIG. 14B is a graph quantifying the melanosomes by stage in sAC$^{FF}$ (FF) and sAC$^{KO}$ (KO) mouse melanocytes (n=15 per condition) *P<0.05, ****P<0.0001.

Figure 14C:
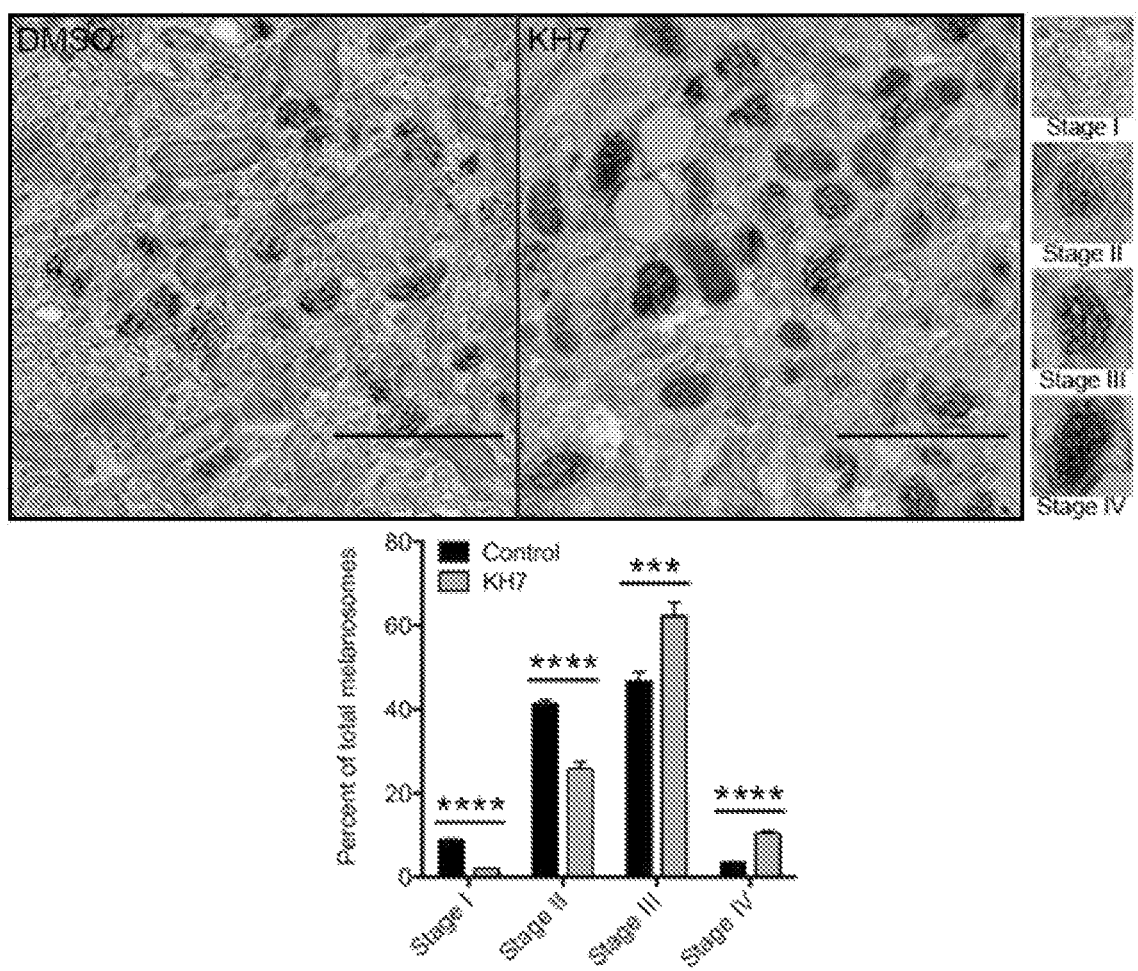
Figure 14D:
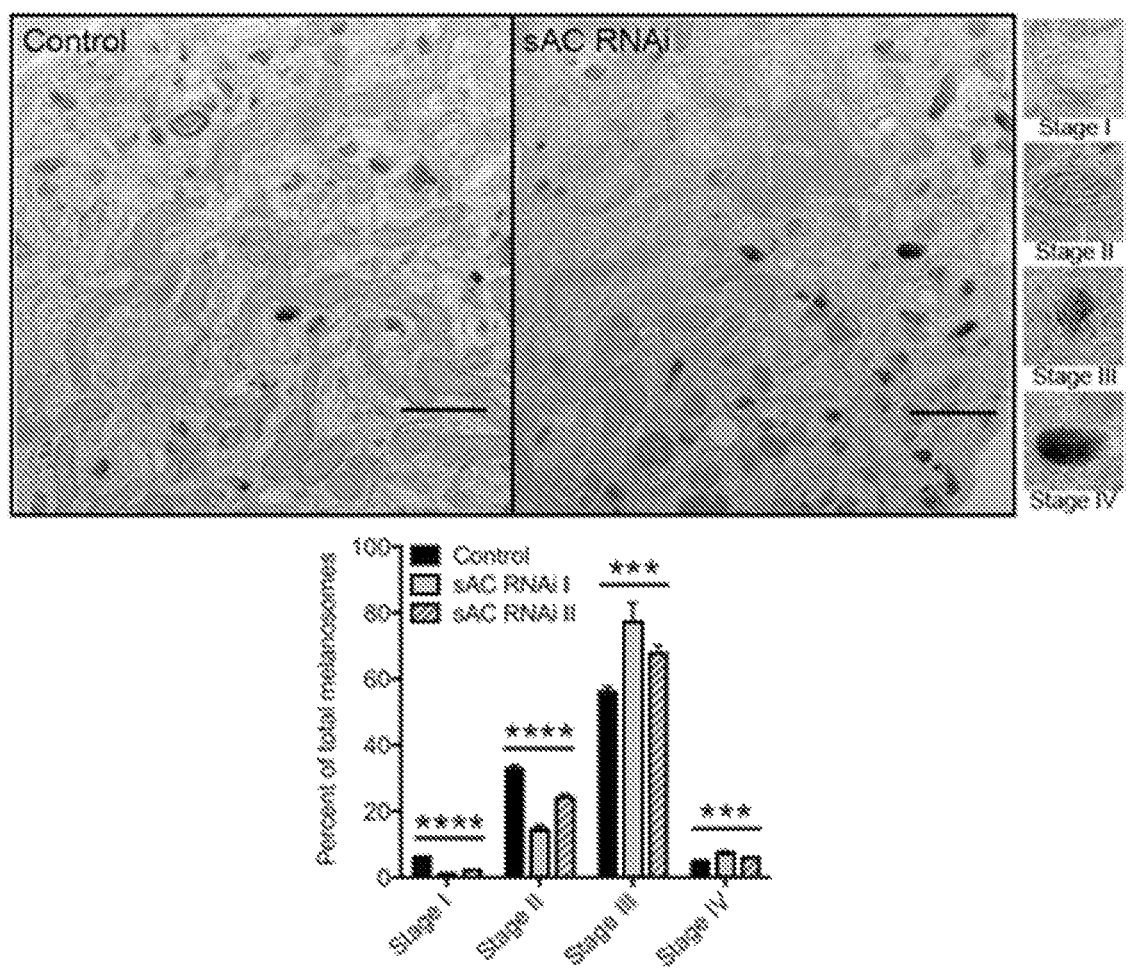

FIG. 14C, top, are electron micrographs of human melanocytes following incubation for two days in vehicle (DMSO, left panel) or KH7 (30 µM, right panel). FIG. 14C, bottom, is a graph of the relative quantitation of melanosome stage following incubation in DMSO or KH7. (n=15 per condition). FIG. 14D, top, are electron micrographs of human melanocytes two days after transfection with control oligos (Control, left panel) or sAC RNAi (10 µM, right panel), Student's t-test *p<0.001, P<0.0001, scale bars, 1 µm. FIG. 14D, bottom, is a graph of the relative quantitation of melanosome stage following transfection with control oligos, sAC RNAi I, or sAC RNAi II. (n=15 per condition), one-way ANOVA, *p<0.001, ****P<0.0001, scale bars, 2 µm.

Figure 15A:
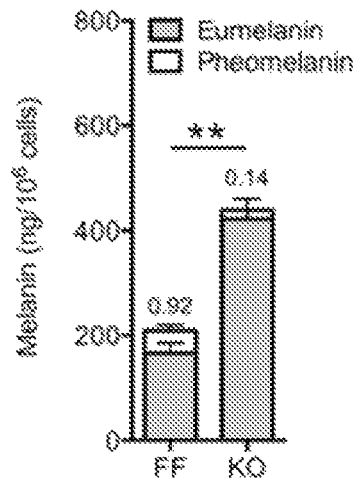
Figure 15B:
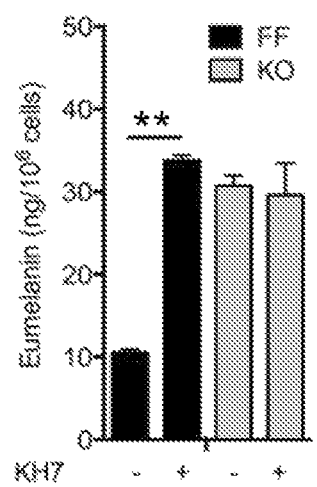
Figure 15C:
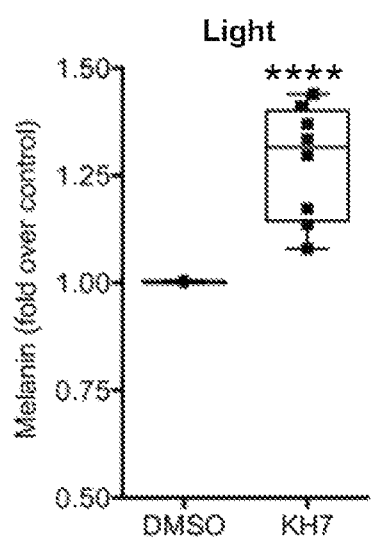
Figure 15D:
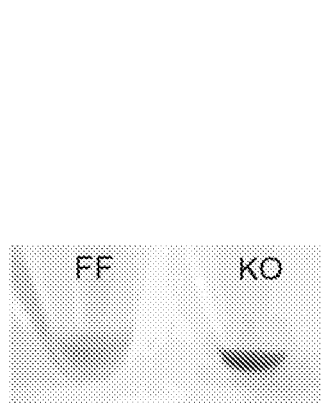
Figure 15E:
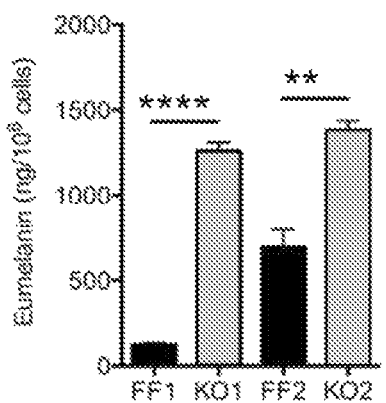
Figure 15F:
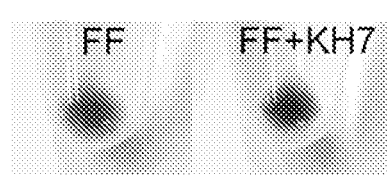
Figure 15G:
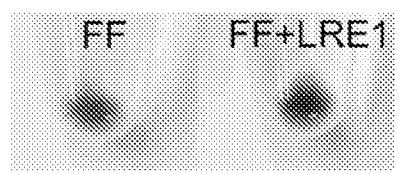
Figure 15H:
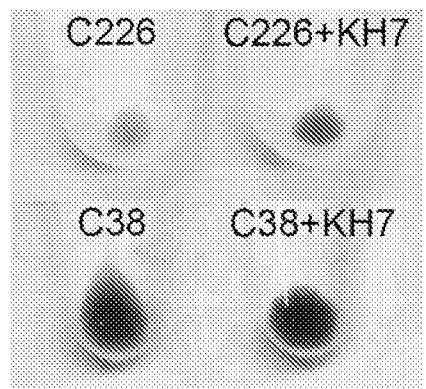
Figure 15I:
Figure 15J:
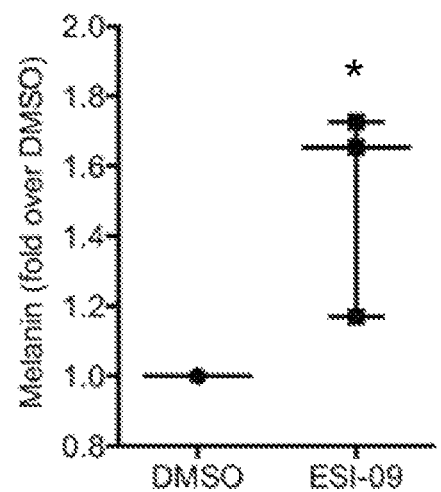

FIGS. 15A-15J provide the results of experiments analyzing the effect of sAC activity on melanin production. FIG. 15A is a graph illustrating the cellular eumelanin and pheomelanin content in sAC$^{FF}$ (FF) and sAC$^{KO}$ (KO) mouse melanocytes. Numbers above bars represent the ratio of pheomelanin to eumelanin. Average of triplicate determinations. FIG. 15B is a graph illustrating the cellular eumelanin content of sAC$^{FF}$ and sAC$^{KO}$ mouse melanocytes grown for 96 hours in the absence (−, DMSO) or presence of KH7 (+, 30 µM). Average of triplicate determinations. FIG. 15C is a graph illustrating the fold over baseline cellular eumelanin level of human melanocytes (n=8) treated with KH7 (30 µM) or vehicle (DMSO) for 48 hours. All assays performed in triplicate. Students t-test P<0.01, **P<0.0001. FIG. 15D is images of cell pellets of sAC$^{FF}$ and sAC$^{KO}$ mouse melanocytes. FIG. 15E is a graph of the melanin levels of pairs of sAC$^{FF}$ and sAC$^{KO}$ mouse melanocytes. FIGS. 15F and 15G are images of cell pellets of sAC$^{FF}$ mouse melanocytes grown in the absence (DMSO, FIGS. 15G and 15F, left panels) or presence of KH7 (FIG. 15G, 30 µM, right panel) or LRE1 (FIG. 15F, 50 µM, right panel) for 96 hours. FIG. 15H is images of cell pellets of human melanocytes (C226, C38) treated with vehicle control (DMSO, left) or KH7 (30 µM, right) for 48 hours. FIG. 15I is images of cell pellets of human melanocytes (C226) treated with vehicle control (DMSO, left) or ESI-09 (10 µM, right) for 48 hours. FIG. 15J is a graph illustrating the fold over baseline cellular (eumelanin) level of human melanocytes treated with ESI-09 (10 µM) or vehicle (DMSO) for 48 hours (n=3, distinct human cell lines). For FIGS. 15E and 15J Students t-test, *p<0.05, p<0.01, **p<0.0001.

FIGS. 16A-16D provide the results of experiments analyzing the in vivo effect of pharmacologic inhibition of sAC. FIG. 16A is images of mice following epilation and treatment with sAC inhibitor (KH7 or LRE1) or vehicle control (DMSO) 3 times daily for 2 weeks. Mice were either treated with DMSO alone on the upper and lower back (left panel) or with sAC inhibitor on the upper back (LRE [middle panel] or KH7[right panel]) and DMSO on the lower back as indicated. Squares below show hair at higher magnification. FIG. 16B is representative examples of hair collected from skin treated with DMSO (left panel), LRE1 (middle panel) or KH7 (right panel). Scale bar, 1 mm. FIG. 16C is a graph illustrating the average ratio of subapical agouti band length to total hair length. Each data point represents the average ratio of ≥10 individual hairs per treatment area per mouse (n=6 or 7 per group). One-way ANOVA. *P<0.05. FIG. 15D are representative photographs of mouse ears and accompanying Fontana-Masson stain after treatment with vehicle (DMSO) on both ears (left panel, n=6), vehicle on the left ear and LRE1 on the right ear (middle panel, n=6), or vehicle on the left ear and KH7 on the right ear (right panel, n=6) twice daily for 2 weeks. White arrow indicates positive Fontana-Masson staining. All topical treatments were performed with 10 µL of 42 mg/ml KH7, 28 mg/ml LRE1, or vehicle alone (DMSO).

DETAILED DESCRIPTION OF THE INVENTION

The invention is based, in part, on the discovery that the soluble adenylyl cyclase (sAC)/exchange protein activated by cAMP (EPAC)-cAMP signaling cascade controls melanosome pH and is a key regulator of melanocyte pigmentation. Therefore, the invention provides methods for modulating melanosome pH and/or melanocyte pigmentation comprising, consisting essentially of, or consisting of administering a sAC/EPAC-cAMP signaling modulator (e.g., a sAC inhibitor, an EPAC inhibitor, a sAC activator, and/or an EPAC activator) to a melanocyte and/or a subject. When the inventive method consists essentially of administering a sAC/EPAC-cAMP signaling modulator additional components can be administered that do not materially affect the efficacy of the modulator (e.g., excipients). When the inventive method consists of administering a sAC/EPAC-cAMP signaling modulator no additional components are administered with the modulator.

sAC is a soluble signaling enzyme that produces cyclic AMP (cAMP), as described in International Patent Application Publication No. WO 2001/085753 and U.S. Pat. No. 6,544,768. The expression of sAC has been observed in keratinocytes, melanocytes, mononuclear cells, eccrine ducts, and nerves of human skin (Zippin et al., *J. Invest. Dermatol.*, 130: 1279-1287 (2010)), in addition to other regions of the body. cAMP mediates cellular responses to nutritional conditions and extracellular signals and has long been known to exert both stimulatory and inhibitory effects on cell growth and proliferation (Dumont et al., *Trends Biochem. Sci.*, 14: 67-71 (1989); Rozengurt et al., *Science*, 234 161-166 (1986)).

As used herein a sAC inhibitor encompasses any substance that inhibits or diminishes the activity of sAC. For example, the sAC inhibitor may directly inhibit or diminish the enzymatic activity of sAC, the sAC inhibitor may inhibit or diminish the expression of sAC, or the sAC inhibitor may alter the activity of an upstream or downstream signaling molecule that affects the activity of sAC.

In certain embodiments of the inventive methods described herein the sAC inhibitor is a small molecule inhibitor of sAC. Any small molecule sAC inhibitor known in the art may be used in the inventive methods described herein. Example of small molecule sAC inhibitors, for use in the inventive method include, but are not limited to, KH7, LRE1, and catechol estrogen 2-hydroxyestradiol. Additional examples of sAC inhibitors for use in the inventive method include the sAC inhibitors disclosed in WO2005070419, WO2006131398, WO2007107384, and WO2008121171, each of which are incorporated herein in their entirety by reference.

In other embodiments of the inventive methods the sAC inhibitor is a nucleic acid molecule that inhibits sAC gene expression. In an embodiment, the nucleic acid molecule directly inhibits sAC gene expression by directly binding to or interacting with sAC mRNA. Examples of nucleic acid inhibitors for use in the invention include, but are not limited to, miRNA, siRNA, and shRNA. In one embodiment the nucleic acid inhibitor comprises the nucleotide sequence of SEQ ID NO: 1 (TCGGAGCATGATTGAAATCGA) (Zippin et al., *J. Biol Chem.*, 288(46): 33283-33291 (2013)).

In another embodiment the sAC inhibitor is a nucleic acid sequence that encodes a dominant negative form of sAC (DN-sAC) The nucleic acid sequence encoding DN-sAC can be administered and expressed in a melanocyte using any method known in the art. In an embodiment, DN-sAC is administered using an expression vector, preferably a viral expression vector.

EPAC is a distinct cAMP effector protein expressed in melanocytes (Baljinnyam et al. *Pigment Cell Melanoma Res.*, 27(4): 611-620 (2014), Baljinnyam et al., *Am J Physiol Cell Physiol.*, 297(4): 802-813 (2009)). EPAC, also known as cAMP-guanine exchange factor (cAMP-GEF), is a cAMP regulated guanine nucleotide exchange factor that can activate Ras family members.

As used herein, an EPAC inhibitor encompasses any substance that inhibits or diminishes the activity of EPAC. For example, the EPAC inhibitor may directly inhibit or diminish the enzymatic activity of EPAC, the EPAC inhibitor may inhibit or diminish the expression of EPAC, or the EPAC inhibitor may alter the activity of an upstream or downstream signaling molecule that affects the activity of EPAC.

In certain embodiments of the inventive methods described herein the EPAC inhibitor is a small molecule inhibitor of EPAC. Any EPAC inhibitor known in the art may be used in the inventive methods disclosed herein. Examples of small molecule EPAC inhibitors, for use in the inventive method include, but are not limited to, 3-(5-tert-butyl-isoxazol-3-yl)-2-((3-chlorophenyl)-hydrazono)-3-oxo-propionitrile (ESI-09), 4-Cyclopentyl-2-(2, 5-dimethyl-benzylsulfanyl)-6-oxo-1,6-dihydropyrimidine-5-carbonitrile (HJC0197), and 4-Methylphenyl-2,4,6-trimethylphenylsulfone) (ESI-05).

In other embodiments of the inventive methods the EPAC inhibitor is a nucleic acid molecule that inhibits EPAC gene expression. For example, the nucleic acid molecule can be a nucleotide sequence that knocksdown (e.g., decreases) EPAC gene expression. In an embodiment, the nucleic acid molecule is a nucleic acid inhibitor that inhibits EPAC gene expression by directly binding to or interacting with EPAC mRNA. Examples of nucleic acid inhibitors for use in the invention include, but are not limited to, miRNA, siRNA, and shRNA.

In another embodiment the EPAC inhibitor is a nucleic acid sequence that encodes a dominant negative form of EPAC (DN-EPAC) The nucleic acid sequence encoding DN-EPAC can be administered and expressed in a melanocyte using any method known in the art. In an embodiment, DN-EPAC is administered using an expression vector, preferably a viral expression vector.

The invention provides a method for increasing the pH of a melanosome in a melanocyte comprising administering a therapeutically effective amount of a sAC inhibitor and/or an EPAC inhibitor to the melanocyte.

The term "increasing the pH" as used herein encompasses any increase in pH compared to a control pH. For example, a change from pH 4 to pH 4.1 is considered an increase in pH. In certain embodiments of the inventive method, the increase in pH is measured compared to the melanocyte and/or subject immediately prior to administration of the inhibitor. Similarly, the term "decreasing the pH" as used herein encompasses any decrease in pH compared to a control pH. For example, a change from pH 7.4 to pH 7.3 is considered a decrease in pH. In certain embodiments of the inventive method the decrease in pH is measured compared to the melanocyte and/or subject immediately prior to administration of the inhibitor.

The invention also provides a method for increasing the amount of melanin in a melanocyte comprising administering a therapeutically effective amount of a sAC inhibitor and/or an EPAC inhibitor to the melanocyte.

Melanocyte, as used herein, refers to any melanin producing cell. Examples of melanocytes in mammals include, but are not limited to, melanin producing cells located in the epidermis of the skin, hair follicles, the middle layer of the eye (e.g., uveal trach), the inner ear, choroid, retinal pigment epithelium, meninges, bones, and heart. In an embodiment, the melanocytes are located in the epidermis of the skin or in a hair follicle.

The melanocyte of any of the inventive methods described herein may be in a subject. The term "subject" as used herein encompasses any living organism (e.g., fungi, bacteria, mammals, birds, fish reptiles, and amphibians). In some embodiments, the subject is a mammal, for example, a mouse, rat, hamster, guinea pig, dog, cat, pig, horse, cow, primate, or human. In a particular embodiment, the subject is a human.

Melanocytes comprise melanosomes, which are organelles that are the site for synthesis, storage, and transport of melanin. Melanosomes mature within the melanocyte in four distinct stages. The first two stages (i.e., Type I and Type II melanosomes) lack pigment, whereas the melanocytes of stages III and IV (i.e., Type III and Type IV melanosomes) contain melanin (see, Raposo et al., *Nat Rev Mol Cell Biol.*, 8(10): 786-797 (2007)). A person of ordinary skill in the art can readily determine the type of melanosome in a melanocyte using routine methods in the art, such as the experimental methods described herein.

Melanin as used herein refers to a natural pigment that is produced in melanosomes by the oxidation of tyrosine. There are three basic types of melanin: eumelanin, pheomelanin, and neuromelanin. A person of ordinary skill in the art can readily determine the type melanin and amount of melanin in a melanocyte and/or melanosome using routine methods in the art. For example, the level of melanin can be analyzed directly using experimental methods described herein or the level of melanin can be analyzed indirectly by measuring the tyrosinase activity of a melanocyte or melanosome.

The invention also provides a method for darkening (i.e., increasing pigmentation) a region and/or organ of a subject comprising administering a therapeutically effective amount of a sAC inhibitor and/or an EPAC inhibitor to the subject. The region and/or organ can be any region and/or organ of the subject wherein increased pigmentation is desired. In some embodiments, the region and/or organ is the eye, epidermis of the skin, or hair follicle.

As used herein "pigmentation" is synonymous with "color" and refers to the natural coloring (e.g., skin color) that is due to the presence of melanin. Thus, for example, increased pigmentation would lead to a darkening of the color of the skin, whereas decreased pigmentation would lead to a lightening of the color of the skin.

The invention also provides a method for treating a disease associated with decreased melanin in a subject comprising administering a therapeutically effective amount of a sAC inhibitor and/or an EPAC inhibitor to the subject.

Examples of diseases associated with decreased melanin include, but are not limited to, albinism, vitiligo, Parkinson's Disease (Xu et al., *Biomolecules*, 5(2): 1122-1142 (2015)), chediak-higashi syndrome, hermansky-pudlak syndrome, piebaldism, waardenburg syndrome, idiopathic guttate hypomelanosis, and progressive macular hypomelanosis.

The invention also provides a method for decreasing the pH of a melanosome in a melanocyte comprising administering a therapeutically effective amount of a sAC activator and/or an EPAC activator to the melanocyte.

Additionally, the invention provides a method for decreasing the amount of melanin in a melanocyte comprising administering a therapeutically effective amount of a sAC activator and/or an EPAC activator to the melanocyte.

The invention also provides a method for lightening (i.e., decreasing pigmentation) a region and/or organ of a subject comprising administering a therapeutically effective amount of a sAC activator and/or an EPAC activator to the subject. The region and/or organ can be any region and/or organ of the subject wherein decreased pigmentation is desired. In some embodiments, the region and/or organ is the eye, epidermis of the skin, or hair follicle.

As used herein a sAC activator encompasses any substance that activates or enhances the activity of sAC. For example, the sAC activator for use in the inventive methods described herein may be a small molecule that directly interacts with sAC and increases its activity. Alternatively, the sAC activator for use in the inventive methods described herein can be a compound that increases the expression or total amount of sAC in a melanocyte. For example, the sAC activator may be a recombinant sAC (rsAC) protein. The rsAC may be a wild-type protein or the rsAC may contain a mutation that increases the enzymatic activity compared to a wild-type sAC. The rsAC protein can be administered to the cell by any methods known in the art. For example, the rsAC can be administered using a plasmid, a viral vector, a cosmid, or an artificial chromosome. Preferably, the rsAC is administered using a viral (e.g., lentiviral, adenoviral, adeno-associated viral, retroviral, herpes-simplex viral) vector.

As used herein an EPAC activator encompasses any substance that activates or enhances the activity of EPAC. For example, the EPAC activator for use in the inventive methods described herein may be a small molecule that directly interacts with EPAC and increases its activity. Alternatively, the EPAC activator for use in the inventive methods described herein can be a compound that increases the expression or total amount of EPAC in a melanocyte. For example, the EPAC activator may be a recombinant EPAC (rEPAC) protein. The EPAC may be a wild-type protein or the rEPAC may contain a mutation that increases the enzymatic activity compared to a wild-type EPAC. The EPAC protein can be administered to the cell by any methods known in the art. For example, the EPAC can be administered using a plasmid, a viral vector, a cosmid, or an artificial chromosome. Preferably, the rsAC is administered using a viral (e.g., lentiviral, adenoviral, adeno-associated viral, retroviral, herpes-simplex viral) vector.

The EPAC activator for use in the inventive methods described herein can also be a small molecule activator. EPAC activators for use in the inventive methods are known in the art and include, but are not limited to small molecule cAMP analogs. Examples of small molecule cAMP analogs include 2'-O-Methyladenosine-3', 5'-cyclic monophosphate (2'-O-Me-cAMP), 8-Bromo-2'-O-methyladenosine-3', 5'-cyclic monophosphate (8-Br-2'-O-Me-cAMP), 8-Bromo-2'-O-methyladenosine-3', 5'-cyclic monophosphate, acetoxymethyl ester (8-Br-2'-O-Me-cAMP-AM), 8-(4-Chlorophenylthio)adenosine-3', 5'-cyclic monophosphate (8-CPT-cAMP), 8-Hydroxy-2'-O-methyladenosine-3', 5'-cyclic monophosphate (8-OH-2'-O-Me-cAMP), 8-(4-Chlorophenylthio)-2'-O-methyladenosine-3', 5'-cyclic monophosphate (8-pCPT-2'-O-Me-cAMP), 8-(4-Chlorophenylthio)-2'-O-methyladenosine-3', 5'-cyclic monophosphate, acetoxymethyl ester (8-pCPT-2'-O-Me-cAMP-AM), 8-(4-Hydroxyphenylthio)-2'-O-methyladenosine-3', 5'-cyclic monophosphate (8-pHPT-2'-O-Me-cAMP), 8-(4-Methoxyphenylthio)-2'-O-methyladenosine-3', 5'-cyclic monophosphate (8-pMeOPT-2'-O-Me-cAMP), 8-Benzylthio-2'-O-methyladenosine-3', 5'-cyclic monophosphorothioate, Sp-isomer (Sp-8-BnT-2'-O-Me-cAMPS/"S-223"), 8-Benzylthioadenosine-3', 5'-cyclic monophosphorothioate, Sp-isomer (Sp-8-BnT-cAMPS/"S-220"), 8-Bromo-2'-O-methyladenosine-3', 5'-cyclic monophosphorothioate, Sp-isomer (Sp-8-Br-2'-O-Me-cAMPS), and 8-(4-Chlorophenylthio)-2'-O-methyladenosine-3', 5'-cyclic monophosphorothioate, Sp-isomer (Sp-8-pCPT-2'-O-Me-cAMPS).

The invention also provides a method for treating a disease associated with increased melanin comprising administering a therapeutically effective amount of a sAC activator and/or an EPAC activator to the subject.

Examples of diseases associated with increased melanin include, but are not limited to, post-inflammatory pigmentation and lentigines.

The art recognizes a strong correlation between the level of melanin in a subject and the susceptibility to develop skin cancer. In particular, subjects with decreased levels of melanin are at a greater risk for developing skin cancer (Scherer et al., *Mutation Research,* 705: 141-153 (2010) and Brenner et al. *Photochemistry and Photobiology,* 84: 539-549 (2008)). Therefore, the invention also provides a method for preventing or decreasing the risk of skin cancer in a subject comprising administering a therapeutically effective amount of a sAC inhibitor and/or an EPAC inhibitor to the subject. The subject for use in the inventive method may be any subject described herein and is preferably a human. In certain embodiments the subject is at a higher risk (e.g., increased susceptibility) for developing skin cancer compared to the risk of the general population, such as a person considered to have light skin color, a person with a family history of skin cancer, or a person with a disease associated with decreased melanin. A person of ordinary skill in the art can readily identify a person who is considered to be at a high risk for developing skin cancer.

The inventive methods described herein can also be usefully employed for cosmetic applications, such as tanning lotions, makeup, or hair coloring. Therefore, the invention also provides a composition comprising a sAC inhibitor and/or an EPAC inhibitor or a sAC activator, and/or an EPAC activator and a cosmetically acceptable carrier.

The route of administration of the sAC/EPAC-cAMP signaling modulator (e.g., a sAC inhibitor, an EPAC inhibitor, a sAC activator, and/or an EPAC activator) is not particularly limited so long as the sAC/EPAC-cAMP signaling modulator (e.g., a sAC inhibitor, an EPAC inhibitor, a sAC activator, and/or an EPAC activator) is able to modulate (e.g., activate or inhibit) sAC or EPAC in the melanocyte. Indeed, although more than one route can be used to administer the modulator, a particular route can provide a more immediate and more effective reaction than another route. Preferably, the modulator is administered topically. A dose of the modulator also can be applied or instilled into body cavities, absorbed through the skin via a transdermal patch, inhaled, ingested, administered to the eye via, for instance, eye drops, or administered parenterally via, for instance, intravenous, intraperitoneal, intraoral, intradermal, subcutaneous, or intraarterial administration.

As used herein "therapeutically effective amount" refers to an amount effective, at dosages and for periods of time necessary to achieve a desired result. The therapeutically effective amount may vary according to factors such as the reason for use and the individual subject. For example a therapeutically effective amount of an EPAC inhibitor or sAC inhibitor is an amount sufficient to increase the pH of a melanosome, increase the level of melanin in a melanocyte, and/or treat a disease associated with increased melanin. Conversely, a therapeutically effective amount of an EPAC activator or sAC activator is an amount sufficient to decrease the pH of a melanosome, decrease the level of melanin in a melanocyte, and/or treat a disease associated with decreased melanin.

As used herein a "cosmetically effective amount" of a modulator refers to an amount effective, at dosages and for periods of time necessary to achieve a desired cosmetic result (e.g., darkening or lightening of skin pigmentation).

As used herein a "prophylactically effective amount" of a modulator refers to an amount effective, at dosages and for periods of time necessary to achieve a desired prophylactic result (e.g., prevention of skin cancer or decreasing the risk of skin cancer).

The sAC/EPAC-cAMP signaling modulator (e.g., a sAC inhibitor, an EPAC inhibitor, a sAC activator, and/or an EPAC activator) of the inventive methods described herein may be administered to the melanocyte and/or subject as a composition comprising a therapeutically effective, prophylactically effective, or cosmetically effective amount of the sAC/EPAC-cAMP signaling modulator (e.g., a sAC inhibitor, an EPAC inhibitor, a sAC activator, and/or an EPAC activator) and a pharmaceutically acceptable excipient. In another aspect, the sAC/EPAC-cAMP signaling modulator may be administered as a composition which comprises a therapeutically effective, cosmetically effective, or prophylactically effective amount of one or more of the modulators, as described above, formulated together with one or more pharmaceutically acceptable excipients and other therapeutically effective medications known in the art allowing for but not limited to combination therapies to improve overall efficacy of each individual therapeutic or to limit the concentration of either therapeutic to avoid side effects and maintain efficacy. The active ingredient (i.e., the modulator(s)) and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically acceptable" or "cosmetically acceptable" is employed herein to refer to those compounds, materials, compositions, and/or dosage forms which are, within the scope of sound medical or cosmetic judgment, suitable for use in contact with the tissues of the subject with toxicity, irritation, allergic response, or other problems or complications, commensurate with a reasonable benefit/risk ratio.

The phrase "pharmaceutically-acceptable excipient" or "cosmetically-acceptable excipient" as used herein are synonymous and refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic or cosmetic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical or cosmetic compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subjects's stomach may be increased by the addition of a disintegrant to the composition. Disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical or cosmetic compositions of the present invention, the modulator of sAC and/or EPAC and any other solid excipients are dissolved or suspended in a liquid carrier such as water, water-for-injection, vegetable oil, alcohol, polyethylene glycol, propylene glycol or glycerin.

Liquid pharmaceutical or cosmetic compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical or cosmetic compositions of the present invention may also contain a viscosity enhancing agent to improve the mouth or skin feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

For topical applications, excipients may include polyethylene glycol ethers of alkyl alcohols having the general formula $CH_3(CH_2)xCH_2(OCH_2CH_2)nOH$ wherein x is 8 to 20, preferably 10 to 16, more preferably 10, 14 or 16, and n is 2 to 100, preferably 2 to 150, more preferably 4 to 100; including:

steareth-20, a polyethylene glycol ether of stearyl alcohol that has the formula $CH_3(CH_2)16CH_2(OCH_2CH_2)nOH$ wherein n=20, and is available commercially as Brij® 78, Alkasurf SA®-20, Brox® S-20, Hodag® Nonionic S-20, Lanycol®-78, Lipocol® S-20, Procol® SA-20, Simulsol® 78, Unicol® SA-20, and Volpo® S-20;

steareth-100, a polyethylene glycol ether of stearyl alcohol that has the formula $CH_3(CH_2)16CH_2(OCH_2CH_2)nOH$ wherein n=100, and is available commercially as Brij® 700, Lanycol®-700, and Volpo® S-100; and ceteareth-20, a polyethylene glycol ether of cetearyl alcohol having the formula $R(OCH_2CH_2)nOH$ wherein R represents alkyl groups derived from cetyl and stearyl alcohols and n=20, and available commercially as Brij® 68, Acconon® W 230, Alkasurf® CA-20, Empilan® KM20, Eumulgin® B-2, Hetoxol® CS-20, Hodag® Nonionc CS-20, Incropol® CS-20, Lipocol® SC-0, Macol® CSA-20, Procol® CS-20, Siponic® E-10, Unicol® CSA-20, and Unimul® B-2.

The excipients for topical application may also include poloxamer 185, copolymers of ethylene oxide and propylene oxide having the formula $HO(C_2H_4O)a(C_3H_6O)b(C_2H_4O)aH$ where a=19 and b=30, and available commercially as Hodag® Nonionic 1065-P, and Pluracare®/Pluronic® P-65;

The excipients for topical application may also include poloxamer 407 copolymers of ethylene oxide and propylene oxide having the formula $HO(C_2H_4O)a(C_3H_6O)b(C_2H_4O)aH$ where a=98 and b=67, and available commercially as Hodag® Nonionic 1127-F, Macol® 27, Pluracare®/Pluronic® F-127, and Synperonic® PE/F127;

For topical applications, solutions, emulsions, gels, creams, ointments, lotions, sticks, pastes, shampoos, foams, patches, mousses, and the like may be used, as are known in the art.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. Some embodiments provide micelles having an average diameter less than about 50 nm, and such as micelles having an average diameter less than about 30 nm, or even less than about 20 nm.

While all suitable amphiphilic carriers are contemplated, examples of particularly suitable carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers are saturated and mono-unsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Some embodiments of polymers are those having a molecular weight of from about 100 or 120 daltons up to about 5,000 or 10,000 daltons, such as about 300 daltons to about 5,000 daltons. In a particular embodiment, the polymer is polyethyleneglycol having a molecular weight of from about 100 to about 5,000 daltons, and more preferably having a molecular weight of from about 300 to about 5,000 daltons. In another embodiment, the polymer is polyethyleneglycol of 750 daltons (PEG (750)). Polymers may also be defined by the number of monomers therein; an embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha, beta, or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259, hereby incorporated herein by reference) and Gramera, et al. (U.S. Pat. No. 3,459,731, hereby incorporated herein by reference) described electroneutral cyclodextrins. Other derivatives include cyclodextrins with cationic properties [Parmeter (II), U.S. Pat. No. 3,453,257, hereby incorporated herein by reference], insoluble crosslinked cyclodextrins (Solms, U.S. Pat. No. 3,420,788, hereby incorporated herein by reference), and cyclodextrins with anionic properties [Parmeter (III), U.S. Pat. No. 3,426,011, hereby incorporated herein by reference]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127, hereby incorporated herein by reference).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 micrometers in diameter; large unilamellar vesicles (LUVS) are typically larger than 0.05 micrometers. Oligolamellar large vesicles and multilamellar vesicles have multiple, usually concentric, membrane layers and are typically larger than 0.1 micrometers. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057, both of which are hereby incorporated herein by reference; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, hereby incorporated herein by reference Release Modifiers The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and and methacrylates).

The following examples further illustrate the invention but, of course, should not be construed as in any way limiting its scope.

Example 1

This example demonstrates that sAC is expressed in human melanocytes and localizes to melanosomes.

To determine the expression pattern of sAC in melanocytes, sAC expression and localization was determined in isolated human primary melanocytes. Briefly, primary human melanocytes derived from neonatal foreskins were obtained from the Yale Dermatology Cell Culture Facility (New Haven, Conn., USA) and grown in Opti-MEM medium supplemented with 5% fetal bovine serum (FBS), 1% penicillin-streptomycin, 10 ng/ml of fibroblast growth factor-2, 1 ng/ml of heparin, 0.1 µM dibutyryl cAMP (dbcAMP), and 0.1 mM 3-isobutyl-1-methylxanthine (IBMX). Prior to experiments, melanocytes were cultured in "cAMP starvation media" without dbcAMP and without IBMX for 24 hours. The expression of sAC mRNA was measured by RT-PCR using the primers 5'-GAGCC-CACCTCCAGGGAAGAAGAGGC-3' (SEQ ID NO: 2) and 5'-GGAGGAGTCCACTGTGGAACTTGAGG-3' (SEQ ID NO: 3) which are directed against exons 25 and 29, respectively. Protein expression was determined by Western blot analysis using the sAC specific antibody R21.

As shown in FIGS. 1A and 1B, sAC mRNA and protein expression was present in melanocytes derived from humans with varied baseline pigmentation levels (e.g., "light" and "dark"). These data show that sAC is expressed in human melanocytes and confirm previous reports identifying sAC expression in human skin (Zippin et al., *J Invest Dermatol.,* 130(5): 1279-1287 (2010); Magro et al., *Arch Pathol Lab Med.,* 136(12): 1558-1564 (2012)).

Immunohistochemistry was performed to determine the localization of sAC within the melanocyte. Briefly, cells were cultured on sterile glass coverslips in 24-mm wells at $50 \times 10^3$ cells/coverslip in "cAMP starvation media" for 48 hours. Cells were then fixed with 3% (w/v) paraformaldehyde for 15 minutes at room temperature, and permeabilized with 0.1% Triton X-100 in Buffer A (125 mM sodium chloride, 10 mM sodium phosphate, 2 mM magnesium chloride) at −20° C. The monoclonal antibodies were used in this study, R21 (1:100) and R52 (1:50) (Zippin et al., *FASEB,* 17: 82-84 (2003)), Tyrosinase (1:100, Santa Cruz Biotechnology, C-19), and TRP1 (1:100, Santa Cruz Biotechnology, G-17). Fluorescence was detected after secondary staining with Alexa Fluor 546 donkey anti-goat IgG antibody (Invitrogen) and Alexa Fluor 647 donkey anti-mouse IgG antibody (Invitrogen). All images were acquired using a Zeiss LSM 880 and analyzed using NIS-Elements AR 4.60 (Nikon).

Immunocytochemical studies revealed a punctate appearance of sAC staining in the cytoplasm of melanocyte lines (FIGS. 1C and 1D). Co-staining with antibodies recognizing the melanosome markers tyrosinase-related protein 1 (TYRP1, TRP1) and tyrosinase identified these punctate structures as melanosomes (FIGS. 1C-1H). Therefore, sAC is localized in close proximity to or is associated with melanosomes.

Taken together, these data demonstrate that sAC is expressed in melanocytes and is localized to the melanosomes within the melanocyte.

Example 2

This example demonstrates that the loss of sAC activity leads to an alkalization of melanosome pH.

To genetically evaluate the role of sAC in melanosome biology, a strain of mice with three exons encoding the second of two catalytic domains of the ADCY10 gene flanked by loxP sites (ADCY10fl/fl) (Chen et al., *Brain Res.,* 1518: 1-8 (2013); Watson et al. *Journal of Experimental Medicine,* 212(7): 1021-1041 (2015)) was utilized to generate immortalized mouse melanocytes by serial passage (Tamura et al., *In Vitro Cell Dev Biol.,* 23(7): 519-522 (1987)). Briefly, newborn mice were euthanized and skin was removed from the back, placed in a Petri dish epidermis side up, and incubated in 2.5 ml Dispase in MEMS overnight at 4° C. The next day the dermis was discarded and the epidermis was incubated in trypsin solution until cells became dissociated. Cells were washed to remove the trypsin solution then cultured in TAV medium [Ham's F12 plus glutamine, Penn/Strep, horse serum 7%, fetal bovine serum 7%, dbcAMP (500 µM), $Na_3VO_4$ (1 µM)]. Once the immortalized line was established the media was changed to normal mouse melanocytes culture media [Opti-MEM medium supplemented with 10% FBS, 7% horse serum, 1% penicillin-streptomycin, 400 µM dbcAMP, 0.3 nM cholera toxin (CT), and 1.6 µM 12-O-tetradecanoylphorbol-13-acetate (TPA)]. To generate ADCY10−/− melanocytes ($sAC^{KO}$), parental ADCY10fl/fl cells were infected with either Ad5-CMV-GFP or Ad5-CMV-CREGFP (VectorBio- Labs, Malvern, Pa.) at 200 MOI. 48 hours after infection cells were FACS sorted for GFP fluorescence and only cells that were in the upper 25% of fluorescence were collected and cultured. Independent pairs of ADCY10fl/fl (sAC$^{FF}$) and ADCY10-/- (sAC$^{KO}$) cells were generated. Genetic deletion of ADCY10 was confirmed by PCR and cAMP accumulation (FIGS. 2D-2E). All experiments using mouse melanocytes were performed between passages 15 and 28. Prior to experiments, melanocytes were cultured in "cAMP starvation media" without dbcAMP and without CT for 96 hours.

As shown in FIGS. 2A-2C, ADCY10fl/fl melanocytes synthesized melanin, displayed normal cAMP signaling, and expressed the melanocyte markers MITF and tyrosinase. Additionally, sAC$^{FF}$ and sAC$^{KO}$ melanocytes grew at identical rates (FIG. 2F).

To determine the pH of the sAC$^{KO}$ and sAC$^{FF}$ melanocytes the pH-sensitive vital dye LysoSensor Yellow/Blue DND-160 (Bellono et al. *Sci Rep.*, 6:26570 (2016)) was used. Briefly, cells were incubated with 1 µM LysoSensor DND-160 (Invitrogen) for 5 minutes at 37° C. Lysosensor was excited at 405 nm and its emission detected at 417-483 nm (W1) and 490-530 nm (W2). The ratio of emissions (W1/W2) in Lysosensor-stained puncta was assigned to a pH value based on a calibration curve generated for each experiment using solutions containing 125 mM KCl, 25 mM NaCl, 24 µM monensin, and varying concentrations of MES to adjust the pH to 4, 4.5, 5.0, 5.5, 6.0, 6.5, 7.0, 7.5. The fluorescence ratio was linear for pH 5.0-7.0.

The results from this study show that organelles in sAC$^{KO}$ melanocytes were more alkaline as compared to sAC$^{FF}$ cells (FIGS. 3A-3C).

LysoSensor cannot be used in fixed cells; thereby, limiting the ability to identify the organelle being measured. Therefore, DAMP, a second pH measurement technique, was employed to both confirm the observations using LysoSensor and determine if melanosome pH was affected by sAC inhibition.

N-{3-[(2,4-dinitrophenyl)amino]propyl}-N-(3-aminopropyl)methylamine dihydrochloride (DAMP) is a weakly basic amine that is taken up in acidic organelles of live cells and which has been used to measure melanosome pH (Bin et al., *PLOS One*, 10(6):e0129273 (2015); Tabata et al., *Cell Tissue Res.*, 332(3): 447-460 (2008)). Cells were cultured on sterile glass coverslips in 24-mm wells at 50×103 cells/ coverslip. Cells were washed with fresh "cAMP starvation media" and incubated with 30 µM DAMP [N-(3-((2,4-dinitrophenyl)amino)propyl)-N-(3-aminopropyl)methylamine], Oxford Biomedical Research) for 30 minutes, fixed with 3% (w/v) paraformaldehyde for 15 minutes at room temperature, and washed with 50 mM ammonium chloride. After permeabilization with 0.1% Triton X-100 in Buffer A at −20° C., the cells were labeled with the supplied anti-DNP antibody (Oxford Biomedical Research) according to kit protocol. Melanosomes were identified using the monoclonal antibody (anti-HMB45, 1:40, Santa Cruz Biotechnology). Fluorescence was detected after secondary staining with Alexa Fluor 546 donkey anti-goat IgG antibody (Invitrogen) and Alexa Fluor 647 donkey anti-mouse IgG antibody (Invitrogen). All quantitative analyses were performed using the Object Count tool in Nikon AR 4.60. For each image, the lower intensity threshold limit of each fluorescence channel was defined as the intensity of the dimmest punctum returned using the 3 points circle threshold tool. The upper intensity threshold limit was set to the maximum value. Equivalent diameter (EqDiameter) was restricted to 1.85-30.00 pixels. Circularity was restricted to 0.20-1.00. Mean fluorescence intensity was measured for all DAMP$^+$ puncta. Melanosomes were identified as HMB45$^+$ puncta. DAMP measurements were only recorded when colocalized with HMB45. Frequency distributions were generated for each sample from mean DAMP fluorescence intensity of DAMP$^+$ melanosomes. All analyses were performed on two replicate coverslips (n≥15 cells per coverslip). Melanosomes were first identified as TRP1$^+$ or tyrosinase$^+$ puncta. sAC$^+$ melanosomes were identified as R52$^+$ or R21$^+$ puncta colocalizing with TRP1$^+$ or tyrosinase$^+$ puncta. The degree of colocalization between sAC and melanosomes was calculated as the number of sAC+ melanosomes divided by the total number of melanosomes and expressed as a percentage.

The results from these studies show that the number of DAMP-positive organelles visualized and the amount of DAMP uptake in melanosomes was significantly reduced in sAC$^{KO}$ relative to sAC$^{FF}$ melanocytes (FIG. 4A). By overlaying DAMP-positive organelles with HMB45-positive organelles, we established that in both sAC$^{FF}$ and sAC$^{KO}$ cell lines approximately 70-80% of the DAMP-positive organelles were melanosomes (FIG. 4B). In addition, the total number of HMB45-positive organelles (i.e., melanosomes) were roughly the same between sAC$^{KO}$ and sAC$^{FF}$ melanocytes (FIG. 4C); hence, loss of sAC does not lead to a change in total melanosomes. Since the majority of acidic organelles in melanocytes are melanosomes (>70%, FIG. 4G), the organelles with elevated pH observed using LysoSensor mostly reflect melanosomes. Additionally, a drastic reduction in DAMP signal at each HMB45-positive organelle in sAC$^{KO}$ versus sAC$^{FF}$ melanocytes (FIGS. 4D and 4E) consistent with an increase in melanosomal pH in sAC$^{KO}$ cells. Intensity differences at each melanosome were specific to DAMP; there was no difference in melanosome HMB45 staining intensity between the cell lines (FIG. 4E, lower panel).

Taken together, these data demonstrate that genetic loss of sAC in mouse melanocytes leads to an elevation of melanosome pH.

Example 3

This example demonstrates that pharmacologic inhibition of sAC activity leads to an alkalization of melanosome pH.

The effect of pharmacologic inhibition of sAC was examined using the pH-sensitive vial dye LysoSensor Yellow/Blue DND-160 assay, described above. Briefly, cultured sAC$^{FF}$ melanocytes were treated for 4 hours with 30 µM KH7, 30 µM LRE1, or control (untreated). The cells were incubated with 1 µM LysoSensor DND-160 (Invitrogen) for 5 minutes at 37° C. Lysosensor was excited at 405 nm and its emission detected at 417-483 nm (W1) and 490-530 nm (W2). The ratio of emissions (W1/W2) in Lysosensor-stained puncta was assigned to a pH value based on a calibration curve generated for each experiment using solutions containing 125 mM KCl, 25 mM NaCl, 24 µM monensin, and varying concentrations of MES to adjust the pH to 4, 4.5, 5.0, 5.5, 6.0, 6.5, 7.0, 7.5. The fluorescence ratio was linear for pH 5.0-7.0.

Similar to the genetic loss of sAC, pharmacologic inhibition of sAC with KH7 (Bitterman et al., *J Pharmacol Exp Ther.*, 347(3): 589-598 (2013)) or LRE1 (Ramos-Espiritu et al., *Nat Chem Biol.*, 12(10): 838-844 (2016)) over a 4-hour period induced an alkaline pH shift in sAC$^{FF}$ organelles, but had no effect in sAC$^{KO}$ cells (FIGS. 5A-5C and FIG. 3B).

These data indicate that loss inhibition of sAC leads to an alkalization of melanocyte pH.

The effect of pharmacologic inhibition of sAC was also measured using the DAMP assay described above. Briefly, Cells were cultured on sterile glass coverslips in 24-mm wells at $50 \times 10^3$ cells/coverslip and treated or not treated for 4 hours with 30 μM KH7 or LRE1. Cells were washed with fresh "cAMP starvation media" and incubated with 30 μM DAMP [N-(3-((2,4-dinitrophenyl)amino)propyl)-N-(3-aminopropyl)methylamine], Oxford Biomedical Research) for 30 minutes, fixed with 3% (w/v) paraformaldehyde for 15 minutes at room temperature, and washed with 50 mM ammonium chloride. After permeabilization with 0.1% Triton X-100 in Buffer A at –20° C., the cells were labeled with the supplied anti-DNP antibody (Oxford Biomedical Research) according to kit protocol. Melanosomes were identified using the monoclonal antibody (anti-HMB45, 1:40, Santa Cruz Biotechnology). Fluorescence was detected after secondary staining with Alexa Fluor 546 donkey anti-goat IgG antibody (Invitrogen) and Alexa Fluor 647 donkey anti-mouse IgG antibody (Invitrogen). All images were acquired using a Zeiss LSM 880 and analyzed using NIS-Elements AR 4.60 (Nikon).

Incubation of $sAC^{FF}$ cells with KH7 for 4 hours led to a reduction in DAMP uptake (alkaline shift in pH) at melanosomes (FIG. 4E), whereas KH7 had no effect on $sAC^{KO}$ cells (FIG. 5C). Of note, KH7 had no effect on HMB45 staining intensity (FIG. 4A, FIG. 4E, and FIG. 5D).

The effect of sAC inhibition on melanosome pH was also assessed in human melanocytes. Primary human melanocytes derived from neonatal foreskins were obtained from the Yale Dermatology Cell Culture Facility (New Haven, Conn., USA) and grown in Opti-MEM medium supplemented with 5% fetal bovine serum (FBS), 1% penicillin-streptomycin, 10 ng/ml of fibroblast growth factor-2, 1 ng/ml of heparin, 0.1 μM dibutyryl cAMP (dbcAMP), and 0.1 mM 3-isobutyl-1-methylxanthine (IBMX). Prior to experiments, melanocytes were cultured in "cAMP starvation media" without dbcAMP and without IBMX for 24 hours. The human melanocytes were treated with KH7, KH7 plus cAMP, or control (untreated) and melanosome pH was measured using the DAMP assay described above.

As shown in FIGS. 6A-6B, treatment of human melanocytes with KH7 led to an alkaline shift in melanosome pH. Taken together, these data demonstrate that pharmacologic inhibition of sAC in melanocytes leads to an elevation of melanosome pH.

Example 4

This example demonstrates that the loss of sAC-generated cAMP is responsible for the alkalization of melanosomes following sAC inhibition.

Experiments were performed to determine whether the elevation of melanosomal pH following sAC inhibition was due to the loss of cAMP. Briefly, since there are multiple cAMP-effector proteins in mammalian cells (Dremier et al., *FEBS Lett.*, 546(1): 103-107 (2003)) a membrane permeable cAMP analog, Sp-8-CPT-cAMPs (CPT-cAMP), that stimulates all known cAMP effector proteins (Christensen et al., *J Biol Chem.*, 278(37): 35394-35402 (2003)) was used. $sAC^{KO}$ and $sAC^{FF}$ mouse melanocytes were incubated in the presence or absence of CPT-cAMP for 4 hours prior to DAMP analysis. In a separate experiment, $sAC^{FF}$ mouse melanocytes and human melanocytes were also treated with or without CPT-cAMP and KH7 for 4 hours prior to DAMP analysis.

The results from these studies show that pharmacologic elevation of cAMP for 4 hours was sufficient to induce an acidic shift in melanosome pH in $sAC^{KO}$ melanocytes (FIG. 7A) but had no effect in $sAC^{FF}$ cells (FIG. 7B). Furthermore, co-incubation of $sAC^{FF}$ mouse melanocytes (FIG. 7C) or human melanocytes (FIGS. 6A-6B) with cAMP mitigated the KH7-induced alkaline shift in melanosome pH but had no effect in the absence of inhibitor (FIGS. 7B and 7D).

These data show that the loss of sAC-generated cAMP is responsible for the observed alkalization of melanosomes following sAC inhibition.

To further determine the specificity of sAC on melanosome, experiments were performed to determine whether non-sAC-dependent, endogenous sources of cAMP could rescue melanosome pH following sAC inhibition. It is well established that MSH stimulates tmAC-dependent production of cAMP within a few minutes (Newton et al., *Peptides* 26(10): 1818-1824 (2005)) and FIGS. 2B and 2E); however, in contrast to CPT-cAMP (FIGS. 6A-6B and FIGS. 7A and 7C), MSH-dependent production of cAMP over 4 hours did not affect melanosome pH following sAC inhibition (FIGS. 8A-8D). One report suggested that MSH-dependent signaling after 48 hours could alter melanosomal pH by regulating the expression of V-ATPase channels (Cheli et al., *J Biol Chem.*, 284(28): 18699-18706 (2009)); however, sAC-dependent regulation of melanosome pH occurs quickly (within 4 hours) and cycloheximide did not block the ability of cAMP to rescue pH following sAC inhibition (FIGS. 9A and 9B). Therefore, sAC regulation of pH does not require new protein synthesis.

Thus, this data demonstrates that sAC- and tmAC-dependent cAMP pathways regulate melanocyte biology in distinct manners.

Additionally, treatment of mouse and human melanocytes for 4 hours with the PKA inhibitors H89 or PKI led to a dramatic reduction in the phosphorylation of PKA targeted proteins; however, these drugs had no effect on melanosome pH (FIGS. 10A-10D). Furthermore, addition of H89 or PKI did not block the cAMP-dependent rescue of melanosome pH in $sAC^{KO}$ melanocytes (FIGS. 10E and 10F). Therefore, PKA does not appear to be the relevant cAMP effector protein for melanosome pH regulation.

Taken together, these data demonstrate that the loss of sAC-generated cAMP is responsible for the alkalization of melanosomes following sAC inhibition.

Example 5

This example demonstrates that modulation of exchange protein activated by cAMP (EPAC) alters melanosome pH.

EPAC is a distinct cAMP effector protein expressed in melanocytes. To investigate whether EPAC is important for the regulation of melanosome pH, the EPAC-specific cAMP competitive antagonist ESI-09 (Zhu et al., *Sci Rep.*, 5: 9344 (2015); Chen et al., *Tetrahedron Lett.*, 54(12): 1546-1549 (2013)) and the EPAC selective cAMP agonist, 8-pHPT-2'-O-Me-cAMP were utilized. Briefly, cells were cultured on sterile glass coverslips in 24-mm wells at $50 \times 10^3$ cells/coverslip and were treated or not treated for 4 hours with 30 μM KH7 or LRE1 in the presence or absence of 500 μM 8-pHPT-2'-O-Me-cAMP or 10 μM ESI-09. ESI-09, similar to sAC inhibitors, elevated melanosome pH in $sAC^{FF}$ and human melanocytes (FIGS. 11A-11E). As a competitive cAMP analog, ESI-09 should only block EPAC activity in the presence of a physiological source of cAMP. Consistent with that premise, ESI-09 had no effect on melanosome pH in $sAC^{KO}$ melanocytes (FIG. 11F); thus, sAC-generated cAMP is required for EPAC-dependent regulation of melanosomal pH. Furthermore, the EPAC selective cAMP agonist, 8-pHPT-2'-O-Me-cAMP (Enserink et al., *Nat Cell Biol.*, 4(11): 901-906 (2002); Yano et al., *J Biol Chem.*, 282(26): 18819-18830 (2007)), was sufficient to induce melanosome acidification in sAC$^{KO}$ melanocytes and mitigate the KH7-induced alkalization of melanosome pH in human and mouse melanocytes (FIGS. 12A-12D).

Taken together, these data demonstrate that EPAC is a modulator of melanosome pH.

Example 6

This example demonstrates that inhibition of sAC or EPAC results in increased melanin level in melanocytes and a higher proportion of stage III/IV melanosomes compared to stage I/II melanosomes.

Melanosomes mature in distinct stages from pre-melanosomes (no melanin) to stage IV melanosomes (high melanin level) (Slominski et al., *Physiol Rev.*, 84(4): 1155-1228 (2004)). Fluctuations in melanosome pH and the establishment of a pH set point are regarded as key events in melanogenesis and have a significant impact on human pigmentation (Wakamatsu et al., *Pigment Cell Melanoma Res.*, 30(3): 372-377 (2017); Ambrosio et al., *Proc Natl Acad Sci USA.*, 113(20): 5622-5627 (2016); Bin et al., *PLOS One*, 10(6): e0129273 (2015); Ito et al., *Pigment Cell Melanoma Res.*, 24(1): 63-74 (2011); Tabata et al., *Cell Tissue Res.*, 332(3): 447-460 (2008); Ancans et al., *Exp Cell Res.*, 268(1): 26-35 (2001)). A more alkaline melanosome pH set point is thought to enhance the maturation of melanosomes via activation of the pH-sensitive, rate-limiting melanin-producing enzyme tyrosinase (Ancans et al., *Exp Cell Res.*, 268(1): 26-35 (2001)).

Since loss of sAC activity leads to an increase in melanosome pH, the effect of sAC inhibition on tyrosinase activity was tested. Briefly, tyrosinase activity of melanocytes was determined by measuring the amount of radioactive H$_2$O produced from L-[Ring-3,5-3H]-Tyrosine as previously described (Ancans et al., *Exp Cell Res.*, 268(1): 26-35 (2001)). Mouse melanocytes were incubated in 6-well plates with "cAMP starvation media" containing 5 µCi/ml L-[Ring-3,5-3H]-Tyrosine (Perkin Elmer) for 8 hours. 1.5 ml of media from each well was removed and centrifuged at 1,200 rpm for 5 minutes. 1 ml of supernatant was combined with 1 ml of 0.1M citric acid containing 10% w/v activated charcoal to remove excess tyrosine, then centrifuged at 12,000 rpm for 5 minutes. 3H activity of the supernatant was determined using a scintillation counter. In human cells, tyrosinase activity with and without pharmacologic inhibition of sAC was performed by incubating cells in 6-well plates with media containing 5 µCi/ml L-[Ring-3,5-3H]-Tyrosine and KH7 (30 µM), LRE1 (30 µM) or DMSO (vehicle control) for 8 hours. 1.5 ml of media from each well was put through the same process as above. In all experiments, media incubated in parallel wells containing no cells was used as a negative control for tyrosinase activity.

The results from these studies show that tyrosinase activity in live mouse melanocytes was higher in sAC$^{KO}$ as compared to sAC$^{FF}$ melanocytes (FIG. 13A), and pharmacologic inhibition of sAC increased tyrosinase activity in human melanocytes within a few hours (FIG. 13B). In contrast, tyrosinase expression was not increased following the loss of sAC activity (FIGS. 2G and 13C). Thus, sAC regulation of melanosome pH is consistent with the altered tyrosinase activity in live cells.

Since tyrosinase activity is a driver of melanosome maturation, electron microscopy (EM) was employed to examine whether loss of sAC altered global melanogenesis in human and murine melanocytes. Cell monolayers were fixed in vitro as previously published (Cohen-Gould et al., *Microscopy Today* 21(3): 36-39 (2013)) with a modified Karmovsky's fix (Ito et al., *Bull Pharm Res Inst.*, 72: 1-6 (1968)) and a secondary fixation in reduced osmium tetroxide (De Brujin et al., *J Ultrastruct Res.*, 42(1): 29-50 (1973). Following dehydration, the monolayers were embedded in an epon analog resin. En face ultrathin sections (65 nm) were contrasted with lead citrate (Venable et al., *J Cell Biol.*, 25: 407-408 (1965) and viewed on a JEM 1400 electron microscope (JEOL) operated at 100 kV. Digital images were captured on a Veleta 2K×2K CCD camera (Olympus-SIS)

While loss of sAC activity did not lead to an overall increase in the total number of melanosomes (FIG. 4C), genetic and pharmacologic inhibition of sAC did reduce the proportion of stage I melanosomes with a concomitant increase in stage III and IV melanosomes (FIGS. 14A-14D). This increase in melanogenesis is consistent with both an elevation in melanosome pH and the increase in in vivo tyrosinase activity following sAC inhibition.

Since the main product of increased tyrosinase activity and melanogenesis is melanin, experiments were performed to determine if sAC activity modulates pigment production. Within a few passages following ADCY10 deletion, sAC$^{KO}$ melanocytes grew noticeably darker (FIGS. 15A and 15D-15J). Darkening of sAC$^{KO}$ melanocytes was the result of an increase in melanin content (FIG. 15A). This observation repeated in multiple sets of paired sAC$^{FF}$ and sAC$^{KO}$ melanocytes (FIGS. 15D-15J) and was not due to increased tyrosinase expression or altered cell growth (FIGS. 15B and 15C).

It has been proposed that alkalization of melanosome pH leads to enhanced eumelanin and reduced pheomelanin production (Wakamatsu et al., *Pigment Cell Melanoma Res.*, 30(3): 372-377 (2017); Ambrosio et al., *Proc Natl Acad Sci USA.*, 113(20): 5622-5627 (2016); Bin et al., *PLOS One*, 10(6): e0129273 (2015); Ito et al., *Pigment Cell Melanoma Res.*, 24(1): 63-74 (2011); Tabata et al., *Cell Tissue Res.*, 332(3): 447-460 (2008); Ancans et al., *Exp Cell Res.*, 268(1): 26-35 (2001)). Consistent with loss of sAC activity elevating melanosome pH, sAC$^{KO}$ melanocytes had both an increase in eumelanin and a decrease in pheomelanin content (FIG. 15A). Treatment of sAC$^{FF}$ melanocytes with the sAC inhibitors KH7 or LRE1 increased eumelanin levels but these inhibitors had no effect on sAC$^{KO}$ cells (FIGS. 15B, 15F, and 15G). Thus, sAC activity influences melanin levels in murine melanocytes.

In human melanocytes, pharmacologic inhibition of sAC led to an increase in eumelanin levels in melanocytes (FIGS. 15C and 15H). Thus, similar to its effects on melanosome pH, sAC activity alters melanocyte pigmentation.

Finally, consistent with EPAC driving sAC-dependent control of melanosome pH, ESI-09 induced an increase in eumelanin level in human melanocytes (FIGS. 15I and 15J).

Taken together, these results demonstrate that inhibition of sAC or EPAC results in increased melanin in melanocytes and an increase on the proportion of stage III/IV melanosomes in a melanocyte.

Example 7

This example demonstrates that inhibition of sAC in vivo leads to increased pigmentation.

sAC inhibitors have demonstrated efficacy in mice (Lee et al., *J Biol Chem.*, 286(48): 41353-41358 (2011)); however, their topical use had not been tested. Therefore, experiments were performed to determine whether inhibition of sAC in animals could alter hair pigmentation. Animal experiments were performed in accordance with approved Institutional Animal Care and Use Committee protocol at Weill Cornell Medicine. Age and gender matched C3H/HeJ mice (female, 7 weeks old) were purchased from The Jackson Laboratory. For the analysis of hair pigmentation, the upper and lower dorsum of each mouse were epilated using hair removal wax. 10 µl of KH7 (42 mg/ml in DMSO), LRE1 (28 mg/ml in DMSO) or DMSO (vehicle control) was topically applied onto the upper back and DMSO was applied to the lower back three times a day over two weeks. These mice were monitored for changes in coat color as the epilated hair grew back. Hair was removed from each treated area after 3 weeks to measure the length of the total hair, apical black tip and subapical agouti (pheomelanin) band under a stereo microscope. Mice were euthanized and the treated skin was submitted to a blinded animal pathologist for histological evaluation of the epidermis and hair follicles. This experiment was performed twice with 3-4 mice per cohort (total n=6-7)

The results from these studies show that Application of either of the two sAC specific inhibitors, KH7 or LRE1, to the skin on the back following depilation led to visual darkening of regrown hair as compared to vehicle control (FIG. 16A). Histologic examination of the skin by two animal pathologists did not reveal any pathological change to the hair follicles or epidermis. Hair color in C3H/HeJ mice reflects the relative melanocyte production of eumelanin (black) and pheomelanin (yellow) in each hair shaft (Ito et al., *Pigment Cell Res.*, 16(5): 434-437 (2003)). Microscopic examination of the hair revealed that sAC inhibition led to an increase in eumelanin production (FIG. 16B). Concomitant with the increase in eumelanin was the reduction in length of the agouti (pheomelanin) band (FIGS. 16B and 16C).

These data demonstrate that sAC inhibitors increase melanin production from follicular melanocytes.

Melanocytes also exist in the epidermis at specific areas of mouse skin (e.g., pinnae) (Nordlund et al., *Dermatol Clin.*, 4(3): 407-418 (1986)); thus, these areas were studied to examine the role of sAC in epidermal pigmentation. For analysis of epidermal pigmentation, using C3H/HeJ mice as above, 20 µl of KH7 (42 g/ml), LRE1 (28 mg/ml) or DMSO (vehicle control) was topically applied on the right ear and DMSO was topically applied on the left ear twice a day for two weeks. Ear skin was monitored daily for irritation and changes in pigmentation. After two weeks, mice were euthanized and the treated skin was submitted to a blinded animal pathologist for histological evaluation of the epidermis and special stains (Fontana Masson). This experiment was performed twice with 3 mice per cohort (total n=6)

Topical application of KH7 or LRE1 induced visual darkening of mouse ear epidermis relative to vehicle control and led to an increase in epidermal melanin accumulation (FIG. 16D). Therefore, similar to isolated melanocytes, inhibition of sAC activity in hair follicle and epidermal melanocytes leads to an increase in melanin production.

These data demonstrate that sAC regulation of melanosome pH and tyrosinase activity leads to increased pigmentation in vivo. Additionally, these data provide evidence that pharmacological modulates of the sAC/EPAC-cAMP cascade (e.g., sAC inhibitors, EPAC inhibitors, sAC activators, and EPAC activators) represent a new class of pigment modulating drugs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for increasing the amount of melanin in a melanin-producing melanocyte in a subject, the method comprising administering a soluble adenylyl cyclase (sAC) inhibitor to the melanocyte in an amount sufficient to increase the amount of melanin in the melanocyte.

2. The method of claim 1, wherein the melanocyte is in an eye or epidermis of the subject or in a hair follicle of the subject.

3. The method of claim 1, wherein the subject is a human.

4. The method of claim 2, wherein pigmentation of the eye, skin, or hair of the subject is increased.

5. The method of claim 1, wherein the sAC inhibitor is a small molecule inhibitor or a sAC specific siRNA.

6. The method of claim 1, wherein the sAC inhibitor is administered topically to an eye, skin, or hair follicle of the subject.

7. A method of treating albinism or vitiligo in a subject with melanin-producing melanocytes, the method comprising administering a therapeutically effective amount of a soluble adenylyl cyclase (sAC) inhibitor to the subject, thereby treating the disease by increasing pigmentation in the subject.

8. The method of claim 7, wherein the subject is a human.

9. The method of claim 7, wherein the sAC inhibitor is a small molecule inhibitor or a sAC specific siRNA.

10. The method of claim 7, wherein pigmentation of an eye, skin, or hair of the subject is increased.

11. The method of claim 7, wherein the disease is albinism.

12. The method of claim 4, wherein the subject has albinism.

13. The method of claim 1, wherein the subject has albinism.

14. The method of claim 4, wherein the subject has vitiligo.

15. The method of claim 1, wherein the subject has vitiligo.

16. The method of claim 7, wherein the disease is vitiligo.

17. The method of claim 4, wherein the subject has skin cancer, Parkinson's Disease, Chediak-Higashi syndrome, Hermansky-Pudlak syndrome, piebaldism, Waardenburg syndrome, idiopathic guttate hypomelanosis, or progressive macular hypomelanosis.

18. The method of claim 1, wherein the subject has skin cancer, Parkinson's Disease, Chediak-Higashi syndrome, Hermansky-Pudlak syndrome, piebaldism, Waardenburg syndrome, idiopathic guttate hypomelanosis, or progressive macular hypomelanosis.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
```

```
<223> OTHER INFORMATION: Synthetic

<400> SEQUENCE: 1
tcggagcatg attgaaatcg a                                            21

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
gagcccacct ccagggaaga agaggc                                       26

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
ggaggagtcc actgtggaac ttgagg                                       26
```